US010610246B2

(12) United States Patent
Brady et al.

(10) Patent No.: US 10,610,246 B2
(45) Date of Patent: Apr. 7, 2020

(54) CLOT RETRIEVAL DEVICE FOR REMOVING CLOT FROM A BLOOD VESSEL

(71) Applicant: Neuravi Limited, Galway (IE)

(72) Inventors: Eamon Brady, County Galway (IE); Brendan Casey, Galway (IE); Michael Gilvarry, County Galway (IE); David Hardiman, Dublin (IE); Kevin McArdle, County Galway (IE); Mahmood Razavi, Irvine, CA (US); David Vale, County Galway (IE)

(73) Assignee: Neuravi Limited, Galway (IE)

( * ) Notice: Subject to any disclaimer, the term of this patent is extended or adjusted under 35 U.S.C. 154(b) by 370 days.

(21) Appl. No.: 14/985,729

(22) Filed: Dec. 31, 2015

(65) Prior Publication Data

US 2016/0106448 A1    Apr. 21, 2016

Related U.S. Application Data

(63) Continuation of application No. 14/629,217, filed on Feb. 23, 2015, now Pat. No. 9,445,829, which is a
(Continued)

(51) Int. Cl.
*A61B 17/221* (2006.01)
*A61F 2/01* (2006.01)
*A61B 17/22* (2006.01)

(52) U.S. Cl.
CPC ............ *A61B 17/221* (2013.01); *A61F 2/013* (2013.01); *A61B 2017/2212* (2013.01); *A61B 2017/2215* (2013.01); *A61B 2017/22034* (2013.01)

(58) Field of Classification Search
CPC ................ A61F 2/013; A61F 2002/016; A61F 2230/0093; A61F 2230/0067;
(Continued)

(56) References Cited

U.S. PATENT DOCUMENTS 2,828,147 A    3/1958 Peiffer
3,361,460 A    1/1968 Jansen
(Continued)

FOREIGN PATENT DOCUMENTS

DE    20 2009 001 951 U1    4/2010
DE    10 2009 056 450 A1    6/2011
(Continued)

OTHER PUBLICATIONS

US 6,348,062 B1, 02/2002, Hopkins (withdrawn)
(Continued)

*Primary Examiner* — Dianne Dornbusch
(74) *Attorney, Agent, or Firm* — Troutman Sanders LLP

(57) ABSTRACT

A clot retrieval device 1 for removing occlusive clot from a blood vessel, the device comprises an inner elongate body 3 having a collapsed delivery configuration and an expanded deployed configuration and an outer elongate body 2 at least partially overlying the inner elongate body 2. The outer elongate body 2 is expandable to a radial extent which is greater than the radial extent of the inner body 3 in the deployed configuration to define a clot reception space 11. The outer elongate body 2 comprises a distal end portion 24,49 and the inner elongate body 3 comprises a main body portion 10 and a distal portion which extends in the deployed configuration towards the outer elongate body 2 to a greater extent than the main body portion. The distal portion 10 of the inner elongate member 3 and the distal end portion 24,49 of the outer elongate body 2 together define a three dimensional protective structure to substantially prevent distal egress of clot or clot fragments from the device.

17 Claims, 20 Drawing Sheets

Related U.S. Application Data continuation of application No. PCT/EP2014/054251, filed on Mar. 5, 2014.

(60) Provisional application No. 61/785,213, filed on Mar. 14, 2013.

(58) Field of Classification Search
CPC .......... A61B 17/221; A61B 2017/2212; A61B 2017/2215; A61B 2017/2217
See application file for complete search history.

(56) References Cited

U.S. PATENT DOCUMENTS

| | | |
|---|---|---|
| 4,455,717 A | 6/1984 | Gray |
| 4,612,931 A | 9/1986 | Dormia |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | Weldon |
| 5,092,839 A | 3/1992 | Kipperman |
| 5,122,136 A | 6/1992 | Guglielmi et al. |
| 5,163,951 A | 11/1992 | Pinchuk |
| 5,171,233 A | 12/1992 | Amplatz |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo |
| 5,387,219 A | 2/1995 | Rappe |
| 5,387,226 A | 2/1995 | Miraki |
| 5,449,372 A | 9/1995 | Schmaltz |
| 5,499,985 A | 3/1996 | Hein et al. |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,639,278 A | 6/1997 | Dereume |
| 5,645,558 A | 7/1997 | Horton |
| 5,653,605 A | 8/1997 | Woehl et al. |
| 5,658,296 A | 8/1997 | Bates |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark |
| 5,769,871 A | 6/1998 | Mers Kelly |
| 5,769,884 A | 6/1998 | Solovay |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,702 A | 6/1999 | Romley et al. |
| 5,911,725 A | 6/1999 | Boury |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull |
| 6,146,404 A | 11/2000 | Kim |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,231,597 B1 | 5/2001 | Deem et al. |
| 6,238,412 B1 | 5/2001 | Dubrul |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 * | 1/2002 | Gilson .................. A61F 2/01 606/200 |
| 6,346,116 B1 | 2/2002 | Brooks et al. |
| 6,348,056 B1 | 2/2002 | Bates |
| 6,350,271 B1 | 2/2002 | Kurz et al. |
| 6,355,057 B1 | 3/2002 | DeMarais |
| 6,361,545 B1 * | 3/2002 | Macoviak .......... A61B 17/12109 606/151 |
| 6,364,895 B1 | 4/2002 | Greenhalgh |
| 6,375,668 B1 | 4/2002 | Gifford et al. |
| 6,383,205 B1 | 5/2002 | Samson et al. |
| 6,383,206 B1 | 5/2002 | Gillick |
| 6,402,771 B1 | 6/2002 | Palmer |
| 6,416,541 B2 | 7/2002 | Denardo |
| 6,425,909 B1 | 7/2002 | Dieck |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,488,701 B1 | 12/2002 | Nolting |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 * | 10/2003 | Makower ............. A61B 1/3137 606/200 |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |

(56) References Cited

U.S. PATENT DOCUMENTS

| | | | |
|---|---|---|---|
| 6,726,703 B2 | 4/2004 | Broome et al. | |
| 6,730,104 B1 | 5/2004 | Sepetka | |
| 6,783,528 B2 | 8/2004 | Vincent-Prestigiacomo | |
| 6,824,545 B2 | 11/2004 | Sepetka | |
| 6,855,155 B2 | 2/2005 | Denardo et al. | |
| 6,878,163 B2 | 4/2005 | Denardo et al. | |
| 6,890,340 B2* | 5/2005 | Duane | A61B 17/12022 606/200 |
| 6,913,612 B2 | 7/2005 | Palmer | |
| 6,913,618 B2 | 7/2005 | Denardo et al. | |
| 6,939,361 B1* | 9/2005 | Kleshinski | A61F 2/013 600/434 |
| 6,953,472 B2 | 10/2005 | Palmer et al. | |
| 6,989,019 B2 | 1/2006 | Mazzocchi | |
| 6,994,718 B2* | 2/2006 | Groothuis | A61B 17/12109 606/200 |
| 7,004,954 B1 | 2/2006 | Voss et al. | |
| 7,004,955 B2 | 2/2006 | Shen | |
| 7,004,956 B2 | 2/2006 | Palmer | |
| 7,008,434 B2 | 3/2006 | Kurz et al. | |
| 7,033,376 B2 | 4/2006 | Tsukernik | |
| 7,041,116 B2 | 5/2006 | Goto | |
| 7,048,758 B2 | 5/2006 | Boyle | |
| 7,058,456 B2 | 6/2006 | Pierce | |
| 7,063,707 B2 | 6/2006 | Bose | |
| 7,083,633 B2 | 8/2006 | Morrill et al. | |
| 7,083,822 B2 | 8/2006 | Brightbill | |
| 7,172,614 B2 | 2/2007 | Boyle et al. | |
| 7,175,655 B1 | 2/2007 | Malaei | |
| 7,179,273 B1 | 2/2007 | Palmer et al. | |
| 7,185,922 B2 | 3/2007 | Takayanagi | |
| 7,220,271 B2 | 5/2007 | Clubb | |
| 7,226,464 B2 | 6/2007 | Gamer et al. | |
| 7,229,472 B2 | 6/2007 | DePalma et al. | |
| 7,288,112 B2 | 10/2007 | Denardo et al. | |
| 7,306,618 B2 | 12/2007 | Demond | |
| 7,314,483 B2 | 1/2008 | Landau | |
| 7,316,692 B2 | 1/2008 | Huffmaster | |
| 7,323,001 B2 | 1/2008 | Clubb | |
| 7,331,976 B2 | 2/2008 | McGuckin, Jr. et al. | |
| 7,344,550 B2 | 3/2008 | Carrison et al. | |
| 7,399,308 B2 | 7/2008 | Borillo et al. | |
| 7,410,491 B2 | 8/2008 | Hopkins | |
| 7,452,496 B2 | 11/2008 | Brady et al. | |
| 7,491,215 B2 | 2/2009 | Vale et al. | |
| 7,491,216 B2 | 2/2009 | Brady | |
| 7,510,565 B2 | 3/2009 | Gilson et al. | |
| 7,534,252 B2 | 5/2009 | Sepetka | |
| 7,556,636 B2 | 7/2009 | Mazzocchi | |
| 7,582,111 B2 | 9/2009 | Krolik et al. | |
| 7,594,926 B2 | 9/2009 | Linder | |
| 7,604,649 B2 | 10/2009 | McGuckin, Jr. et al. | |
| 7,604,650 B2 | 10/2009 | Bergheim | |
| 7,609,649 B1 | 10/2009 | Bhandari et al. | |
| 7,618,434 B2 | 11/2009 | Santra | |
| 7,662,165 B2 | 2/2010 | Gilson et al. | |
| 7,670,356 B2 | 3/2010 | Mazzocchi | |
| 7,678,123 B2 | 3/2010 | Chanduszko | |
| 7,691,121 B2 | 4/2010 | Rosenbluth | |
| 7,691,124 B2 | 4/2010 | Balgobin | |
| 7,708,770 B2 | 5/2010 | Linder | |
| 7,717,929 B2 | 5/2010 | Fallman | |
| 7,736,385 B2 | 6/2010 | Agnew | |
| 7,758,606 B2 | 7/2010 | Streeter et al. | |
| 7,766,934 B2 | 8/2010 | Pal | |
| 7,771,452 B2 | 8/2010 | Pal | |
| 7,780,694 B2 | 8/2010 | Palmer | |
| 7,811,305 B2* | 10/2010 | Balgobin | A61B 17/12022 606/191 |
| 7,815,659 B2 | 10/2010 | Conlon | |
| 7,819,893 B2 | 10/2010 | Brady et al. | |
| 7,828,815 B2 | 11/2010 | Mazzocchi | |
| 7,833,240 B2 | 11/2010 | Okushi et al. | |
| 7,846,176 B2 | 11/2010 | Mazzocchi | |
| 7,846,175 B2 | 12/2010 | Bonnette et al. | |
| 7,850,708 B2 | 12/2010 | Pal | |
| 7,887,560 B2 | 2/2011 | Kusleika | |
| 7,901,426 B2 | 3/2011 | Gilson et al. | |
| 7,914,549 B2 | 3/2011 | Morsi | |
| 7,922,732 B2 | 4/2011 | Mazzocchi | |
| 7,927,784 B2 | 4/2011 | Simpson | |
| 7,931,659 B2 | 4/2011 | Bose et al. | |
| 7,998,165 B2 | 8/2011 | Huffmaster | |
| 8,002,822 B2 | 8/2011 | Glocker et al. | |
| 8,021,379 B2 | 9/2011 | Thompson et al. | |
| 8,021,380 B2 | 9/2011 | Thompson et al. | |
| 8,043,326 B2 | 10/2011 | Hancock et al. | |
| 8,048,151 B2 | 11/2011 | O'Brien et al. | |
| 8,052,640 B2 | 11/2011 | Fiorella et al. | |
| 8,057,497 B1 | 11/2011 | Raju et al. | |
| 8,066,757 B2 | 11/2011 | Ferrera et al. | |
| 8,070,791 B2 | 12/2011 | Ferrera et al. | |
| 8,088,140 B2 | 1/2012 | Ferrera et al. | |
| 8,100,935 B2 | 1/2012 | Rosenbluth et al. | |
| 8,109,941 B2 | 2/2012 | Richardson | |
| 8,118,829 B2 | 2/2012 | Carrison et al. | |
| 8,118,856 B2 | 2/2012 | Schreck | |
| 8,123,769 B2 | 2/2012 | Osborne | |
| 8,137,377 B2 | 3/2012 | Palmer et al. | |
| 8,142,422 B2 | 3/2012 | Makower et al. | |
| 8,142,442 B2 | 3/2012 | Palmer et al. | |
| 8,187,298 B2 | 5/2012 | Pal | |
| 8,246,641 B2 | 8/2012 | Osborne et al. | |
| 8,246,672 B2 | 8/2012 | Osborne | |
| 8,252,017 B2 | 8/2012 | Paul, Jr. et al. | |
| 8,252,018 B2 | 8/2012 | Valaie | |
| 8,287,538 B2* | 10/2012 | Brenzel | A61B 17/7225 606/62 |
| 8,298,257 B2 | 10/2012 | Sepetka et al. | |
| 8,357,178 B2 | 1/2013 | Grandfield et al. | |
| 8,357,179 B2 | 1/2013 | Grandfield et al. | |
| 8,357,893 B2 | 1/2013 | Xu et al. | |
| 8,361,095 B2 | 1/2013 | Osborne | |
| 8,366,663 B2 | 2/2013 | Fiorella et al. | |
| 8,409,215 B2 | 4/2013 | Sepetka | |
| 8,414,482 B2* | 4/2013 | Belson | A61F 2/01 600/200 |
| 8,419,748 B2 | 4/2013 | Valaie | |
| 8,460,312 B2 | 6/2013 | Bose et al. | |
| 8,460,313 B2 | 6/2013 | Huffmaster | |
| 8,486,104 B2 | 7/2013 | Samson et al. | |
| 8,529,596 B2 | 9/2013 | Grandfield et al. | |
| 8,574,262 B2 | 11/2013 | Ferrera et al. | |
| 8,574,915 B2 | 11/2013 | Zhang et al. | |
| 8,579,915 B2 | 11/2013 | French et al. | |
| 8,585,713 B2 | 11/2013 | Ferrera et al. | |
| 8,608,761 B2 | 12/2013 | Osborne et al. | |
| 8,679,142 B2 | 3/2014 | Slee et al. | |
| 8,696,622 B2 | 4/2014 | Fiorella et al. | |
| 8,702,652 B2 | 4/2014 | Fiorella et al. | |
| 8,702,704 B2 | 4/2014 | Shelton, IV et al. | |
| 8,702,724 B2 | 4/2014 | Olsen et al. | |
| 8,777,919 B2 | 7/2014 | Kimura et al. | |
| 8,777,979 B2* | 7/2014 | Shrivastava | A61B 17/1214 606/200 |
| 8,784,434 B2 | 7/2014 | Rosenbluth et al. | |
| 8,784,441 B2 | 7/2014 | Rosenbluth et al. | |
| 8,795,305 B2 | 8/2014 | Martin et al. | |
| 8,795,317 B2 | 8/2014 | Grandfield et al. | |
| 8,795,345 B2 | 8/2014 | Grandfield et al. | |
| 8,814,892 B2 | 8/2014 | Galdonik et al. | |
| 8,814,925 B2 | 8/2014 | Hilaire et al. | |
| 8,870,941 B2 | 10/2014 | Evans et al. | |
| 8,900,265 B1 | 12/2014 | Ulm, III | |
| 8,920,358 B2 | 12/2014 | Levine et al. | |
| 8,939,991 B2 | 1/2015 | Krolik et al. | |
| 8,945,143 B2 | 2/2015 | Ferrera et al. | |
| 8,945,169 B2 | 2/2015 | Pal | |
| 8,945,172 B2 | 2/2015 | Ferrera et al. | |
| 8,956,399 B2 | 2/2015 | Cam et al. | |
| 8,968,330 B2 | 3/2015 | Rosenbluth et al. | |
| 9,011,481 B2 | 4/2015 | Aggerholm | |
| 9,039,749 B2 | 5/2015 | Shrivastava et al. | |
| 9,072,537 B2* | 7/2015 | Grandfield | A61B 17/221 |

(56) References Cited

U.S. PATENT DOCUMENTS

| | | |
|---|---|---|
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Imamura et al. |
| 9,254,371 B2 | 2/2016 | Martin et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2* | 2/2017 | Beckham ......... A61B 17/12113 |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2* | 3/2018 | Marchand ......... A61B 17/12022 |
| 9,939,361 B2 | 4/2018 | Gajji et al. |
| 2001/0001315 A1 | 5/2001 | Bates |
| 2001/0016755 A1 | 8/2001 | Addis |
| 2001/0037141 A1 | 11/2001 | Yee et al. |
| 2001/0049554 A1 | 12/2001 | Ruiz |
| 2001/0051810 A1* | 12/2001 | Dubrul ................ A61B 17/221 606/159 |
| 2002/0004667 A1 | 1/2002 | Adams et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1* | 4/2002 | Brady ................ A61F 2/013 606/200 |
| 2002/0049468 A1 | 4/2002 | Streeter et al. |
| 2002/0052620 A1 | 5/2002 | Barbut |
| 2002/0058911 A1* | 5/2002 | Gilson .................. A61F 2/013 604/96.01 |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |
| 2003/0040772 A1 | 2/2003 | Huyodoh et al. |
| 2003/0050663 A1 | 3/2003 | Khachin |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0108224 A1 | 9/2003 | Broome |
| 2003/0171769 A1 | 9/2003 | Barbut |
| 2003/0176884 A1 | 9/2003 | Berrada et al. |
| 2003/0187495 A1* | 10/2003 | Cully .................. A61F 2/013 623/1.15 |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wilson |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachin et al. |
| 2004/0098050 A1 | 5/2004 | Foerster |
| 2004/0133231 A1 | 7/2004 | Maitland |
| 2004/0138692 A1 | 7/2004 | Phung et al. |
| 2004/0153118 A1 | 8/2004 | Clubb |
| 2004/0215318 A1 | 10/2004 | Kwitkin |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |

(56) References Cited

U.S. PATENT DOCUMENTS

| | | |
|---|---|---|
| 2005/0090779 A1 | 4/2005 | Osypka |
| 2005/0090857 A1* | 4/2005 | Kusleika ................ A61F 2/013 606/200 |
| 2005/0125024 A1 | 6/2005 | Sepetka |
| 2005/0171566 A1 | 8/2005 | Kanamaru |
| 2005/0192627 A1 | 9/2005 | Whisenant |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs |
| 2005/0251209 A1 | 11/2005 | Saadat |
| 2005/0267491 A1 | 12/2005 | Kellett et al. |
| 2005/0273135 A1 | 12/2005 | Chanduszko |
| 2005/0288686 A1 | 12/2005 | Sepetka |
| 2006/0008332 A1 | 1/2006 | Greenberg |
| 2006/0009798 A1* | 1/2006 | Callister .......... A61B 17/12022 606/200 |
| 2006/0009799 A1* | 1/2006 | Kleshinski ......... A61B 17/0057 606/200 |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1* | 12/2006 | Shimon .................... A61F 2/01 606/200 |
| 2007/0032879 A1 | 2/2007 | Levine et al. |
| 2007/0088383 A1 | 4/2007 | Pal et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0244505 A1 | 10/2007 | Gilson et al. |
| 2007/0270902 A1 | 11/2007 | Slazas et al. |
| 2008/0045881 A1 | 2/2008 | Teitelbaum et al. |
| 2008/0077227 A1 | 3/2008 | Ouellette |
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1* | 5/2008 | Greenhalgh ....... A61B 17/0057 606/200 |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0200946 A1 | 8/2008 | Braun |
| 2008/0200947 A1 | 8/2008 | Kusleika |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1* | 11/2008 | Farmiga .................. A61F 2/01 606/200 |
| 2008/0312681 A1 | 12/2008 | Ansel |
| 2009/0024157 A1 | 1/2009 | Anukhin |
| 2009/0030443 A1 | 1/2009 | Buser |
| 2009/0069828 A1 | 3/2009 | Martin |
| 2009/0076539 A1 | 3/2009 | Valaie |
| 2009/0088793 A1 | 4/2009 | Bagaoisan |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszki et al. |
| 2009/0149881 A1 | 6/2009 | Vale et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le |
| 2009/0292297 A1 | 11/2009 | Ferrere |
| 2009/0292307 A1 | 11/2009 | Razack |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0054504 A1 | 5/2011 | Wolf et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213403 A1 | 9/2011 | Aboytes |
| 2011/0224707 A1* | 9/2011 | Miloslavski ......... A61B 17/221 606/159 |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0089216 A1 | 4/2012 | Rapaport et al. |
| 2012/0101510 A1 | 4/2012 | Lenker et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Catteneo |
| 2012/0296362 A1 | 11/2012 | Cam et al. |
| 2013/0030461 A1 | 1/2013 | Marks et al. |
| 2013/0046330 A1* | 2/2013 | McIntosh ................ A61F 2/013 606/200 |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0158592 A1 | 6/2013 | Porter |

(56) References Cited

U.S. PATENT DOCUMENTS

| | | |
|---|---|---|
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0183077 A1 | 7/2014 | Rosendall et al. |
| 2014/0194919 A1 | 7/2014 | Losordo et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0112376 A1 | 4/2015 | Molaei et al. |
| 2015/0133990 A1 | 5/2015 | Davidson |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Cale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| EP | 2 301 450 A | 3/2011 |
| EP | 2628455 A1 | 8/2013 |
| JP | 0919438 A1 | 1/1997 |
| JP | 2005-1445 A | 1/2005 |
| JP | 2014-511223 A | 5/2014 |
| WO | WO 94/24926 | 11/1994 |
| WO | WO 97/27808 | 8/1997 |
| WO | 1997/038631 A1 | 10/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 02/02162 | 1/2002 |
| WO | WO 02/11627 | 2/2002 |

(56) References Cited

FOREIGN PATENT DOCUMENTS

| WO | WO 02/43616 | 6/2002 |
|---|---|---|
| WO | WO 02/070061 | 9/2002 |
| WO | WO 02/094111 | 11/2002 |
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2004/056275 A1 | 7/2004 |
| WO | 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | 2006/135823 A2 | 12/2006 |
| WO | WO 2007/054307 | 5/2007 |
| WO | WO 2007/068424 | 6/2007 |
| WO | WO 2008/034615 | 3/2008 |
| WO | 2008/051431 A1 | 5/2008 |
| WO | WO 2008/131116 | 10/2008 |
| WO | 2009/031338 A1 | 3/2009 |
| WO | WO 2009/076482 | 6/2009 |
| WO | WO 2009/086482 | 7/2009 |
| WO | 2009/105710 A1 | 8/2009 |
| WO | WO 2010/010545 | 1/2010 |
| WO | WO 2010/046897 A1 | 4/2010 |
| WO | 2010/075565 A2 | 7/2010 |
| WO | 2010/102307 A1 | 9/2010 |
| WO | WO 2010/146581 A1 | 12/2010 |
| WO | WO 2011/013556 A1 | 2/2011 |
| WO | 2011/066961 A1 | 6/2011 |
| WO | 2011/082319 A1 | 7/2011 |
| WO | WO 2011/095352 A1 | 8/2011 |
| WO | 2011/110316 A1 | 9/2011 |
| WO | WO 2012/052982 A1 | 4/2012 |
| WO | 2012/064726 A1 | 5/2012 |
| WO | WO 2012/081020 A1 | 6/2012 |
| WO | 2012/110619 A1 | 8/2012 |
| WO | WO 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | WO 2013/109756 A2 | 7/2013 |
| WO | 2014/047650 A1 | 3/2014 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/134625 A1 | 9/2015 |
| WO | 2015/161365 A1 | 10/2015 |
| WO | 2015/179324 A2 | 11/2015 |
| WO | 2015/189354 A1 | 12/2015 |
| WO | 2016/010995 A1 | 1/2016 |

OTHER PUBLICATIONS

International Search Report and Written Opinion for International Application No. PCT/EP2014/054251, dated Apr. 9, 2014 (14 pages).
Non-Final Office Action dated Jun. 26, 2018 issued in corresponding U.S. Appl. No. 14/985,823.
Final Office Action issued in corresponding U.S. Appl. No. 14/985,574 dated Jan. 18, 2019.
Non-Final Office Action issued in corresponding U.S. Appl. No. 14/985,877 dated Mar. 29, 2018.
Notice of Allowance issued in corresponding U.S. Appl. No. 14/985,823 dated Mar. 6, 2019.
International Search Report and Written Opinion for corresponding International Application No. PCT/EP2014/054251 dated Apr. 9, 2014.
Office Action issued in corresponding U.S. Appl. No. 14/985,574 dated Jul. 22, 2019.
Extended European Search Report for corresponding EP Application No. 18210248.3 dated Sep. 20, 2019.

* cited by examiner

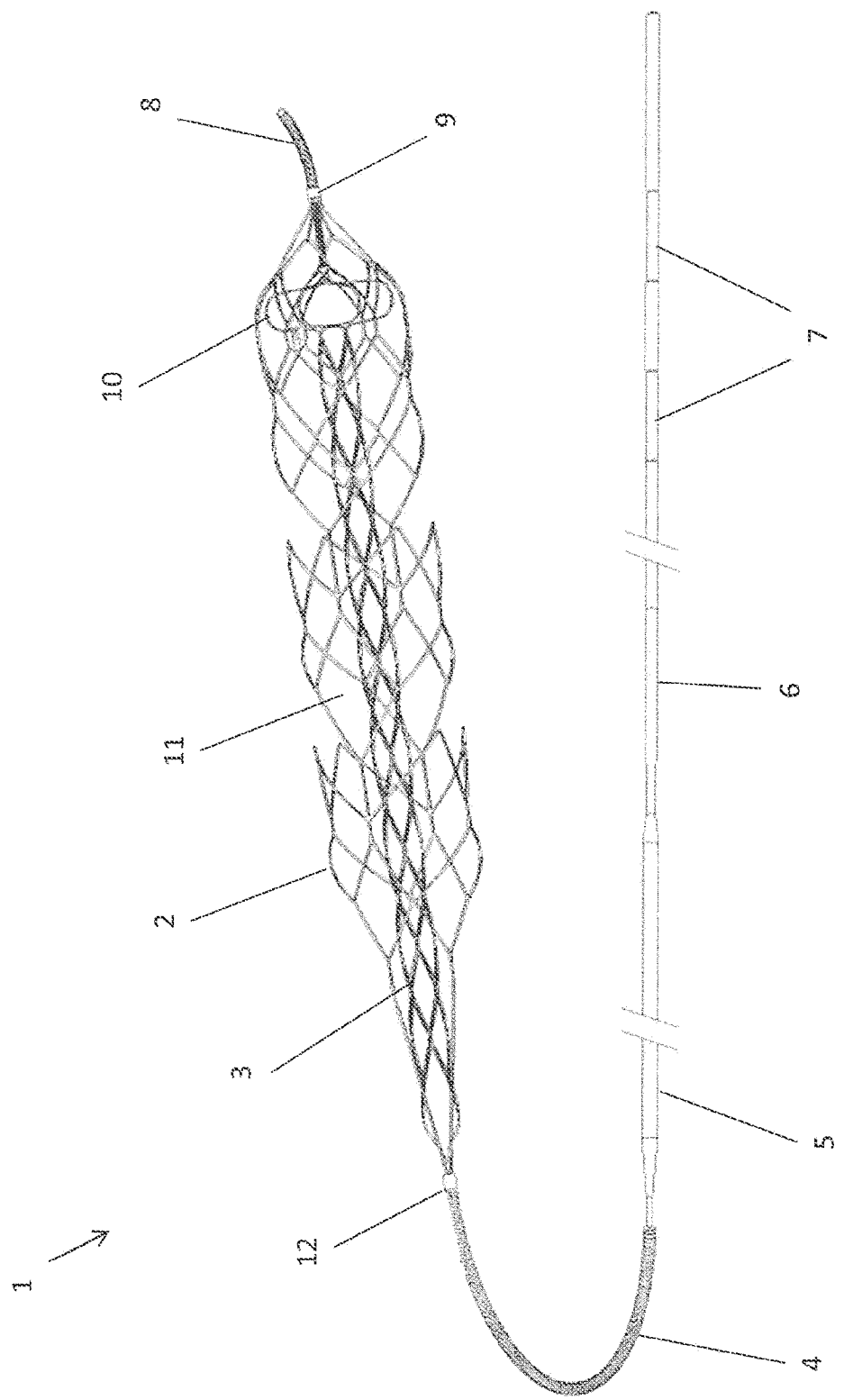

Section A-A

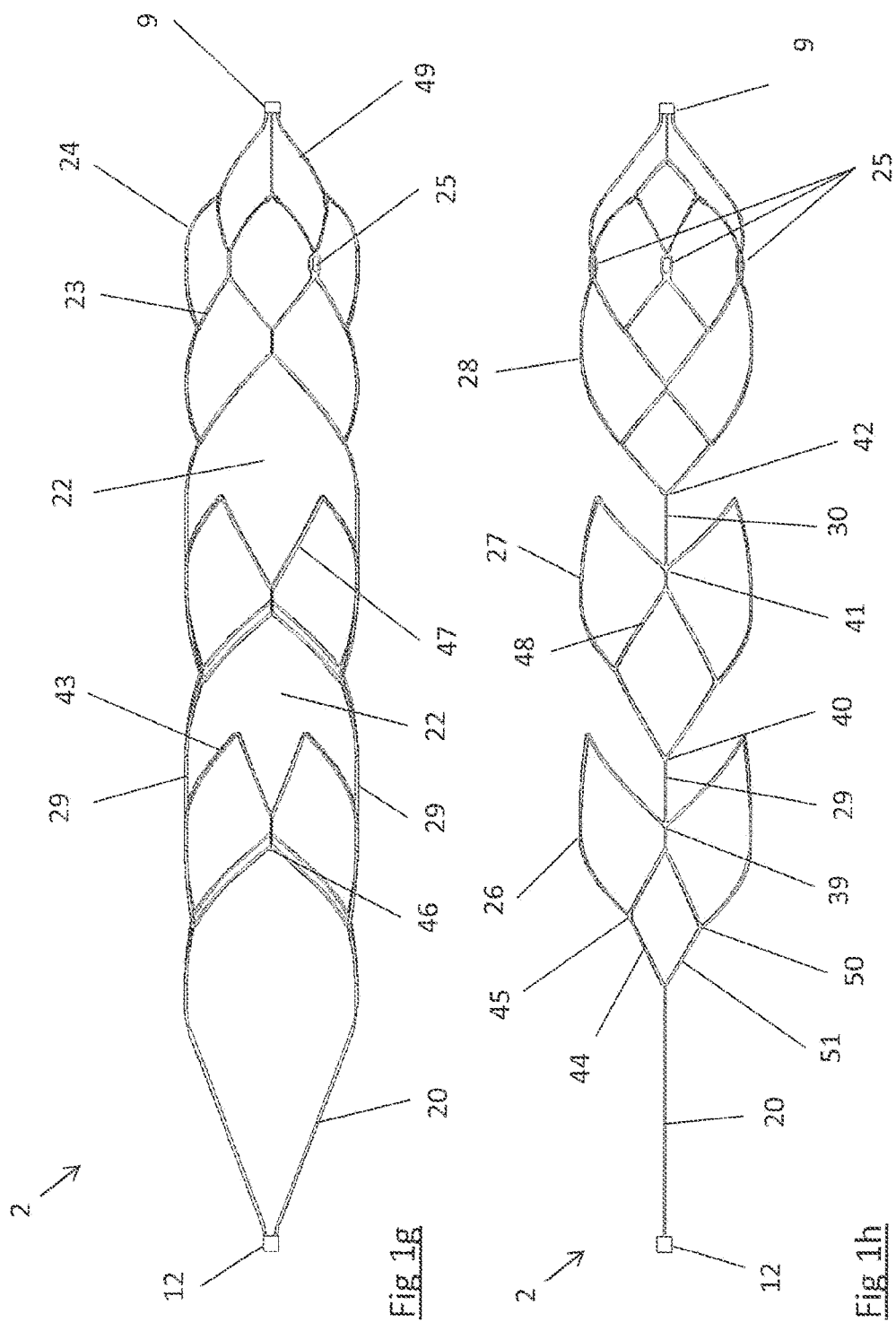

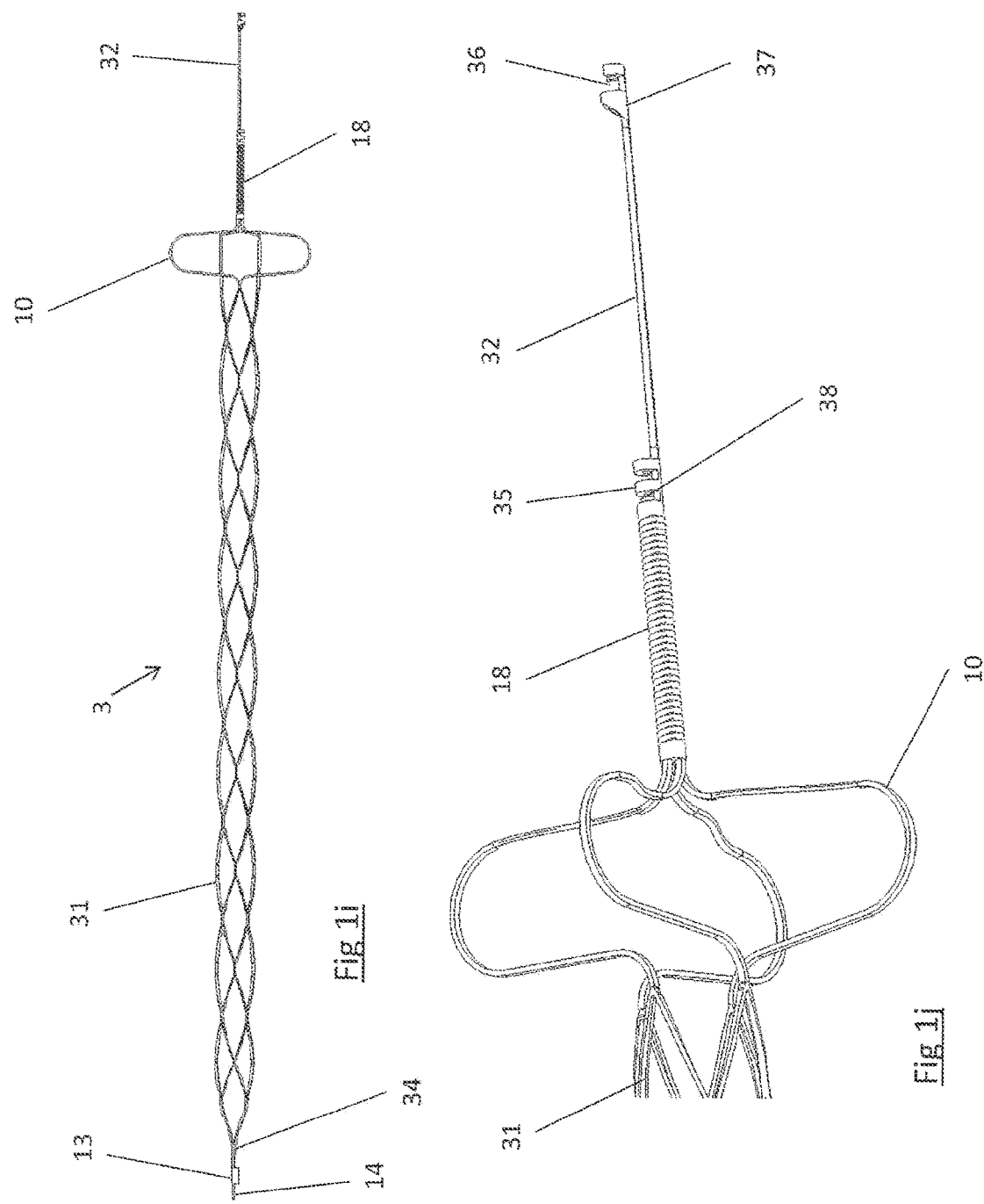

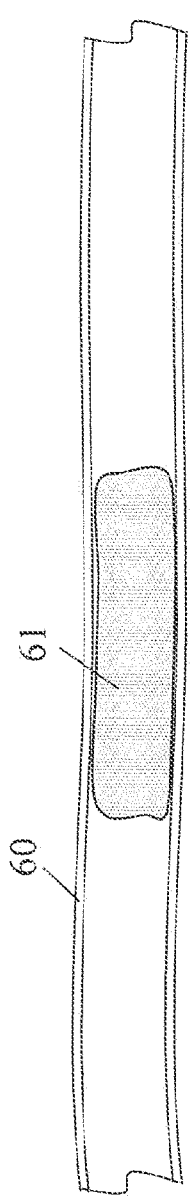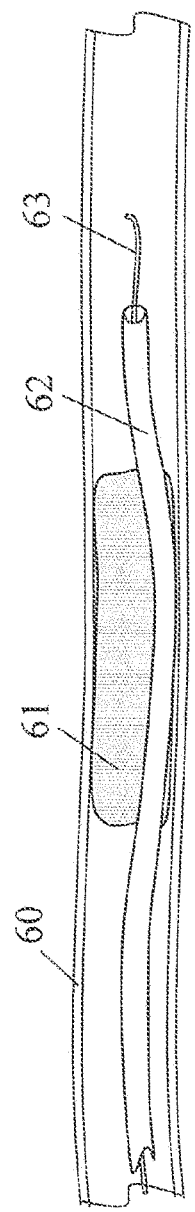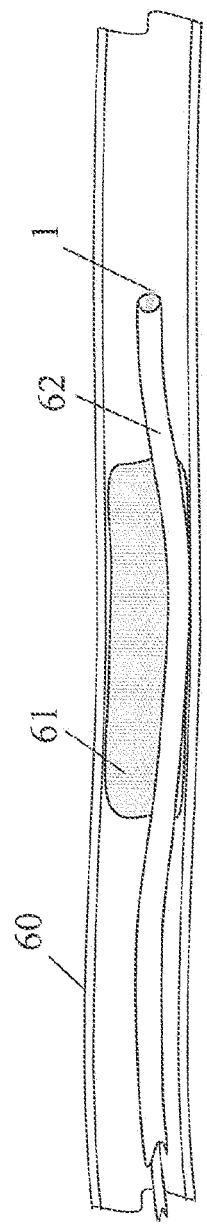

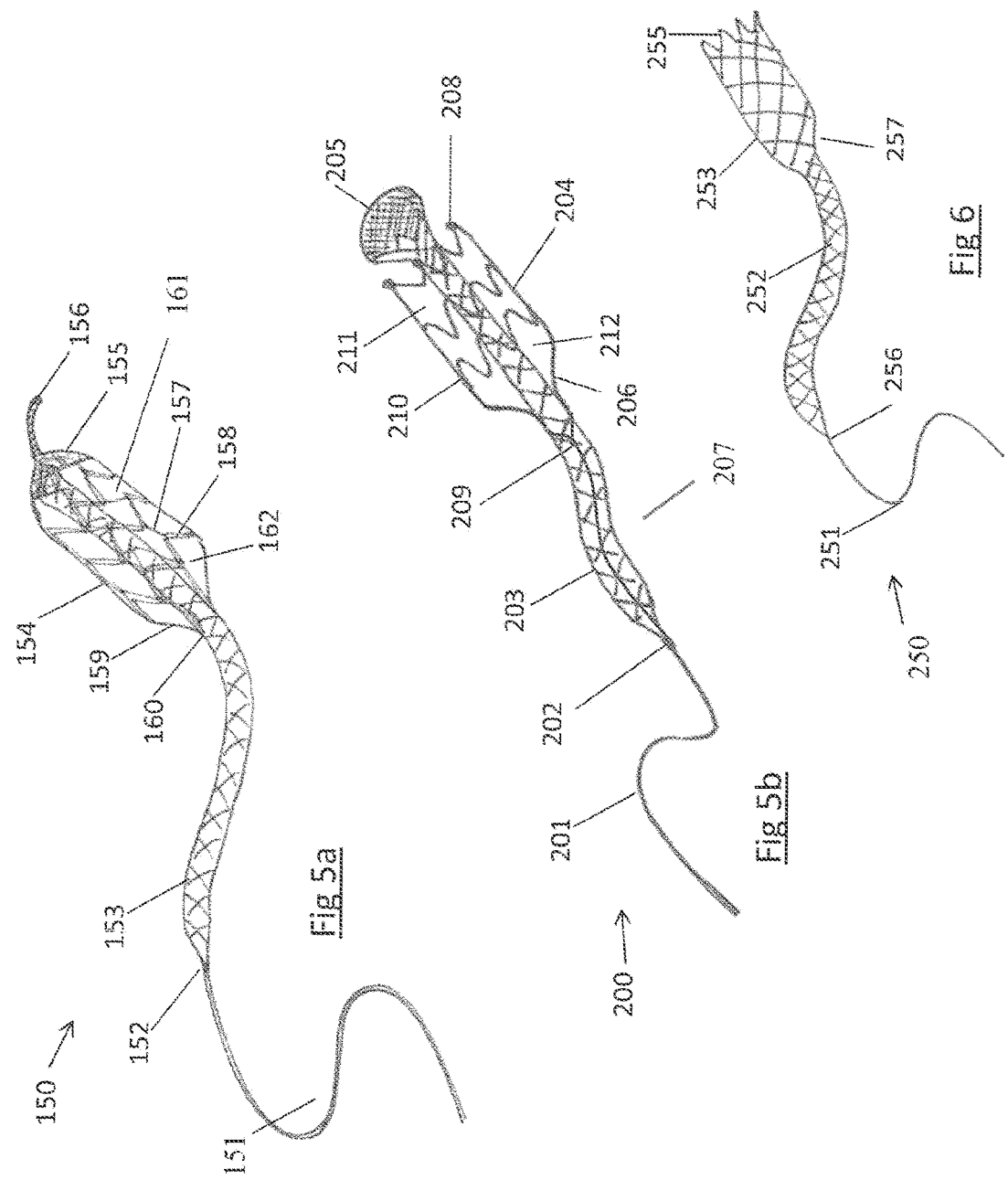

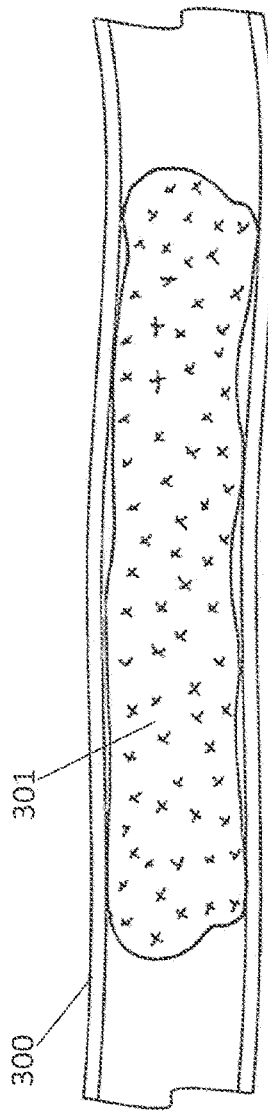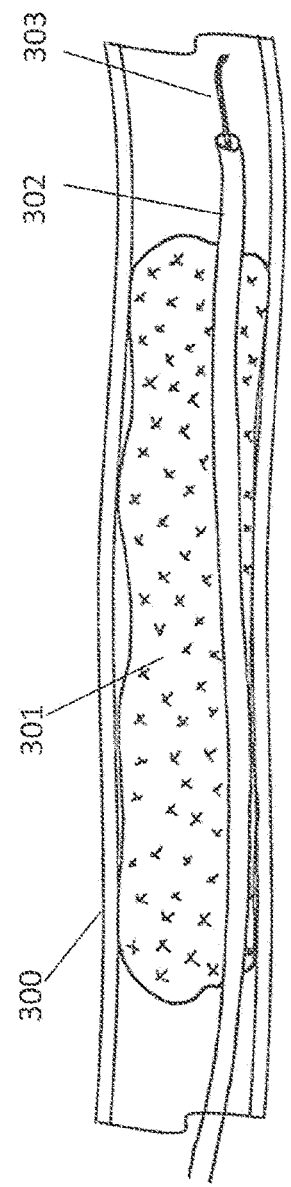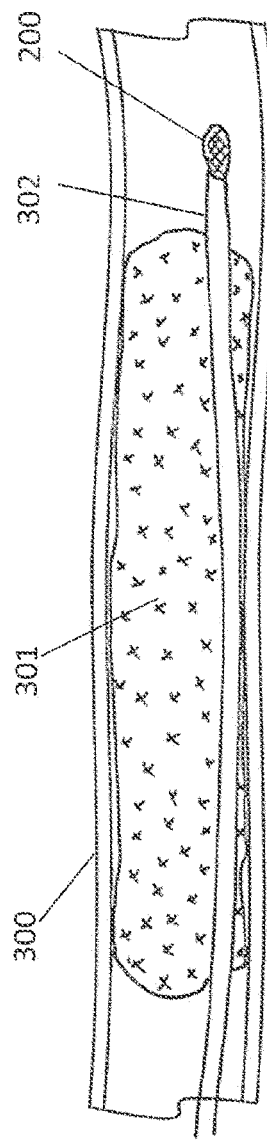

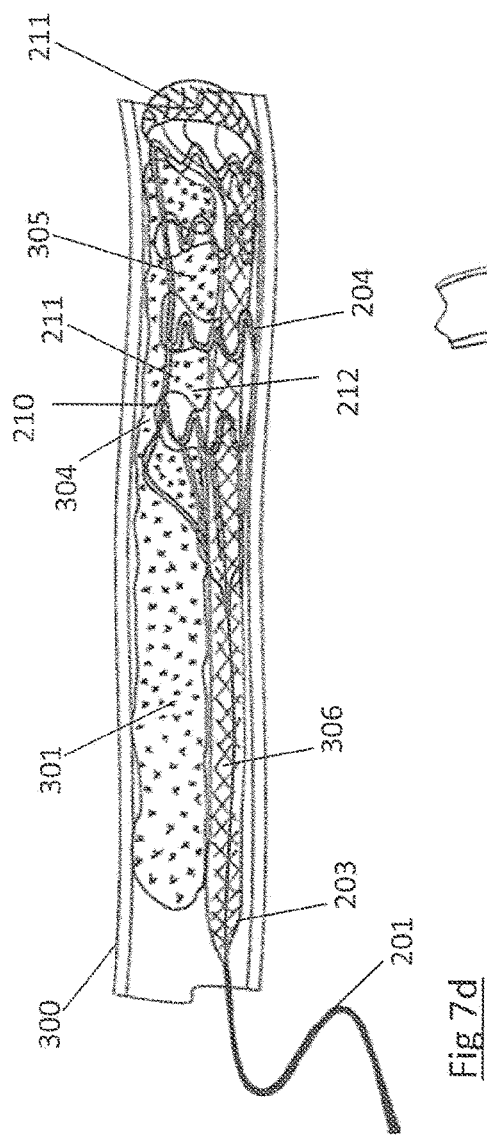

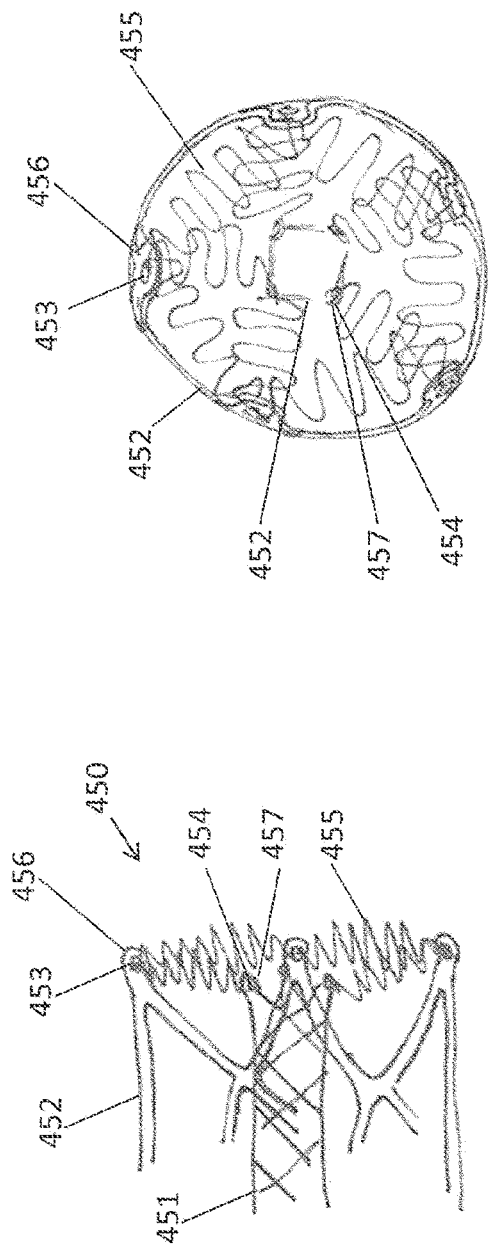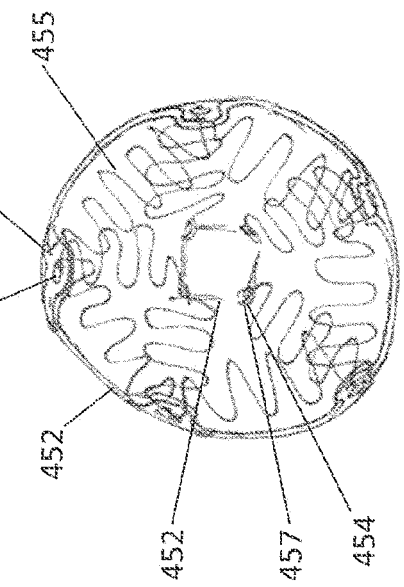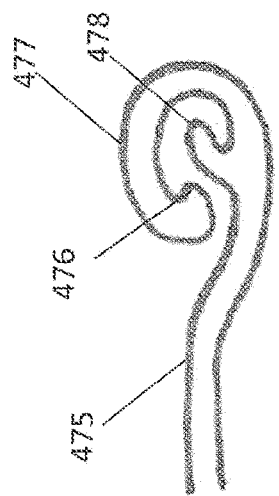

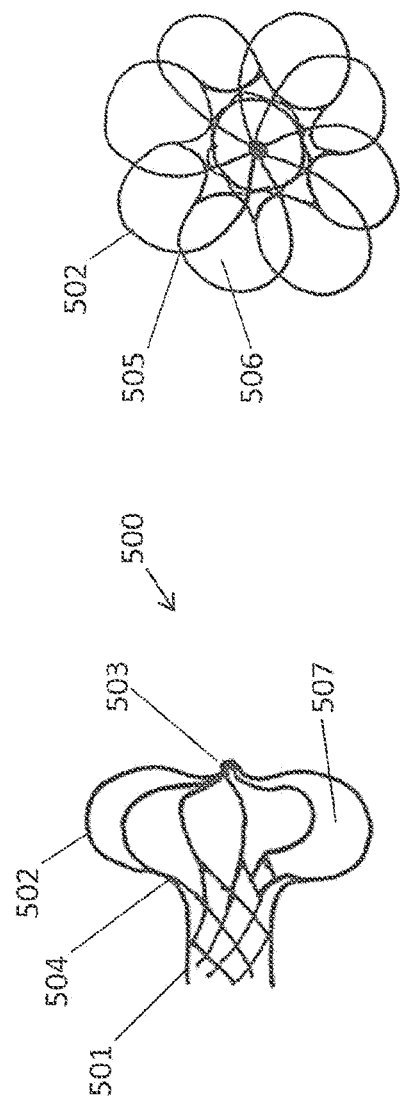
Fig 11a
Fig 11b
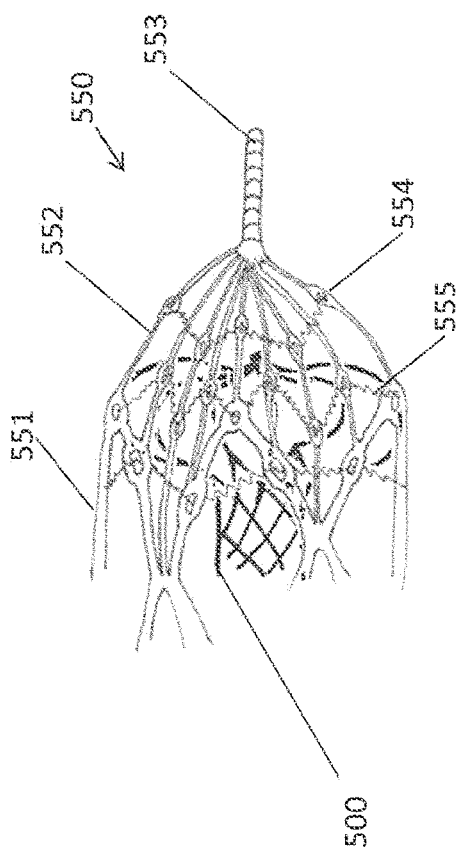
Fig 12

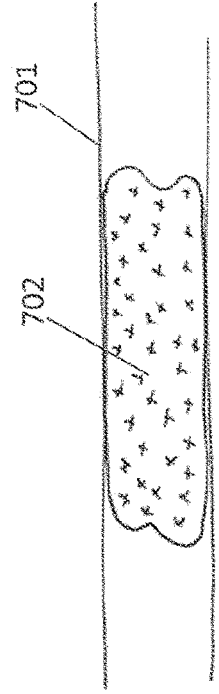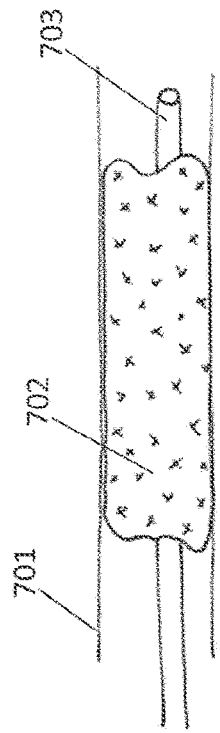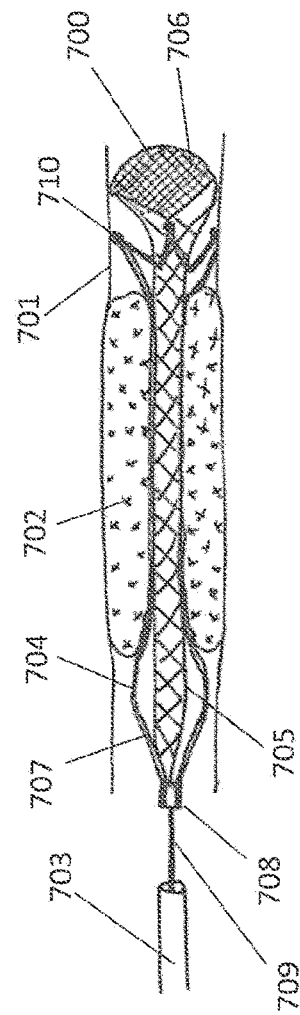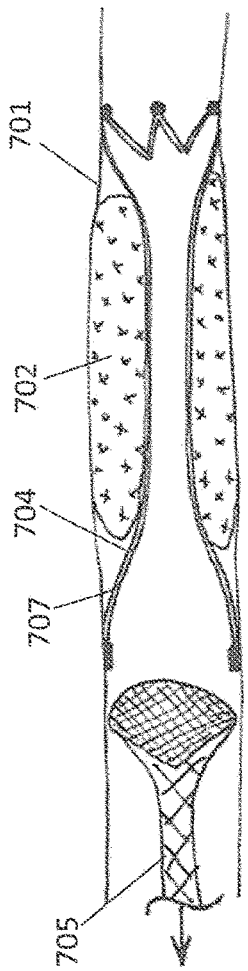
Fig 15a
Fig 15b
Fig 15c
Fig 15d

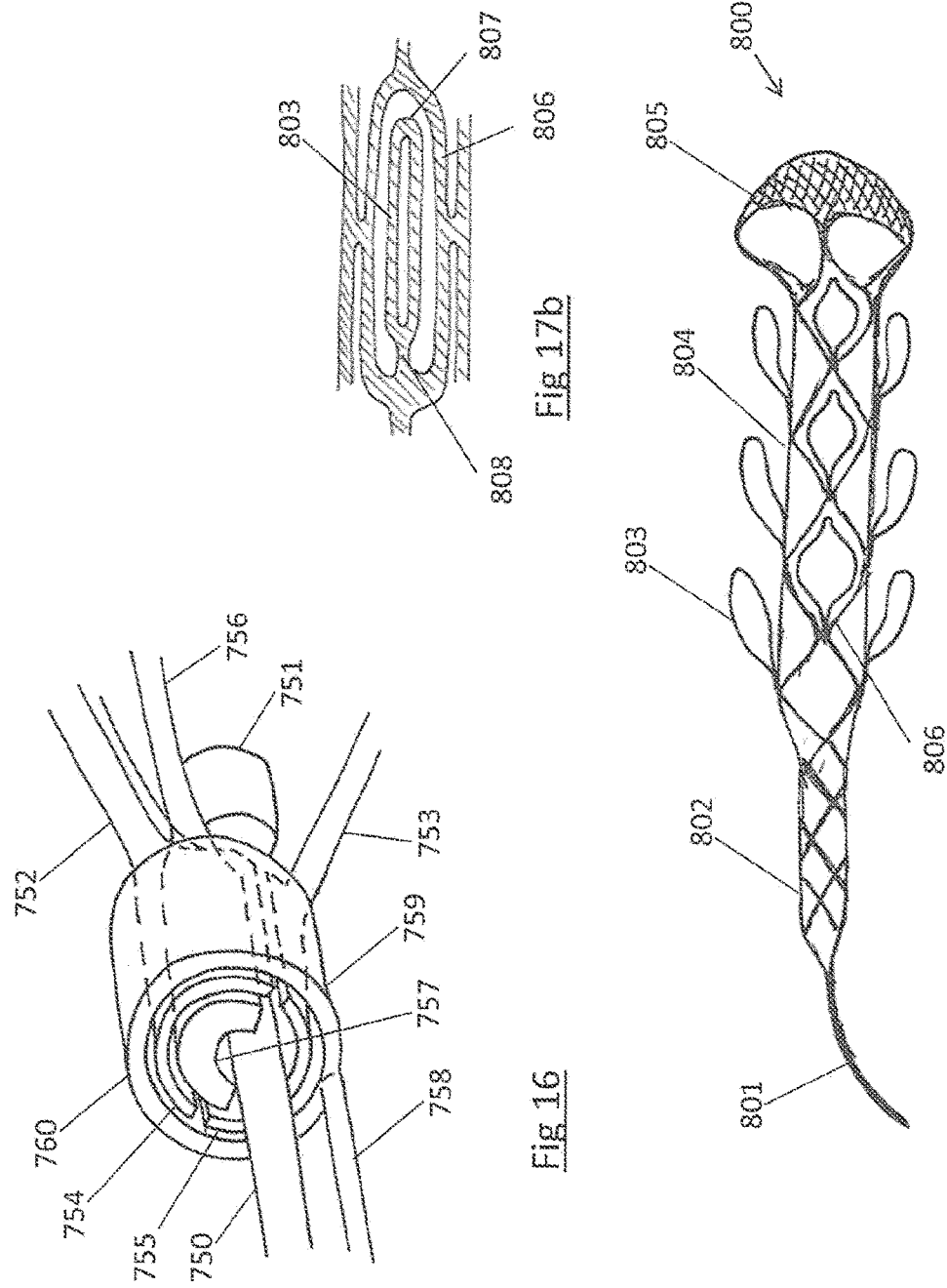

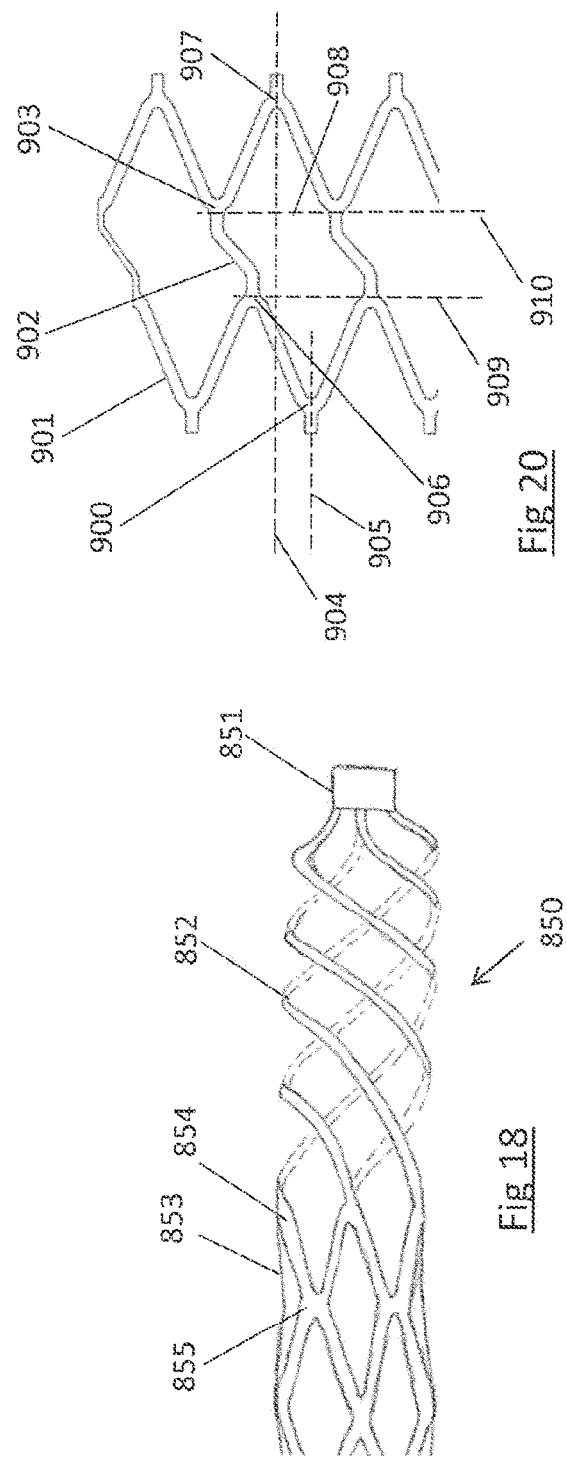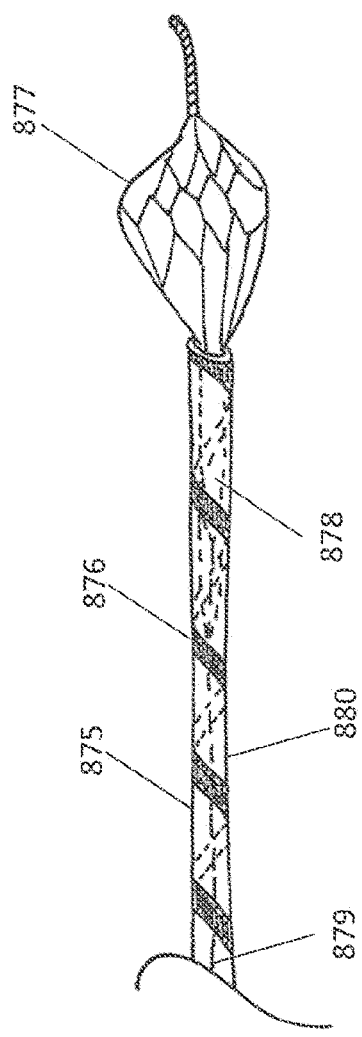
Fig 20
Fig 18
Fig 19

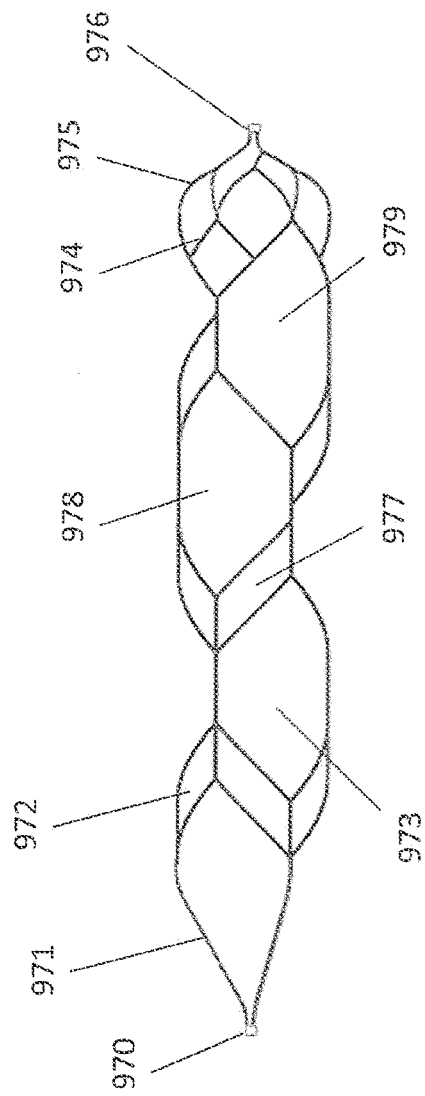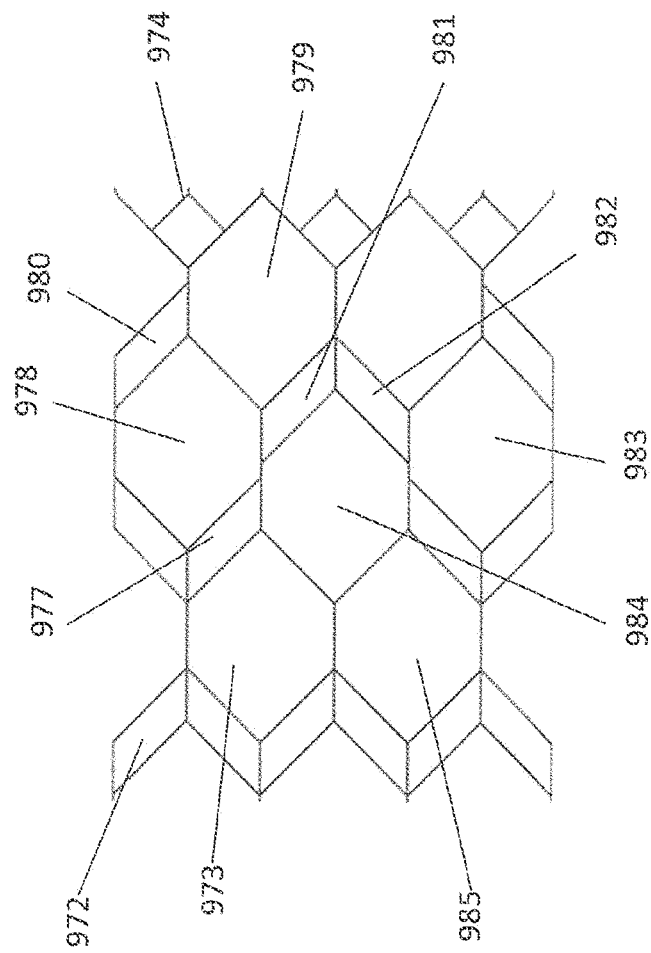
Fig 21a
Fig 21b

CLOT RETRIEVAL DEVICE FOR REMOVING CLOT FROM A BLOOD VESSEL

CROSS-REFERENCE TO RELATED APPLICATIONS

This application is a continuation of U.S. Application No. 14/629,217, filed Feb. 23, 2015, now U.S. Pat. No. 9,445,829 and issued Sep. 20, 2016, which is a continuation of International Application No. PCT/EP2014/054251, filed Mar. 5, 2014, which claims the benefit of priority of U.S. Provisional Application No. 61/785,213, filed Mar. 14, 2013, each of which is incorporated herein by reference in its entirety.

FIELD OF THE INVENTION

This invention relates to devices and methods of removing acute blockages from blood vessels. The invention especially relates to removing acute obstructions from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from pulmonary arteries in patients suffering from pulmonary embolism (PE), from coronary native or graft vessels in patients suffering from myocardial infarction (MI), and from other peripheral arterial and venous vessels in which clot is causing an occlusion.

BACKGROUND

There are significant challenges associated with designing clot removal devices that can deliver high levels of performance:

There are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty. The tortuosity challenge is even more severe in the arteries approaching the brain. For example it is not unusual at the distal end of the internal carotid artery that the device will have to navigate a vessel segment with a 180° bend, a 90° bend and a 360° bend in quick succession over a few centimetres of vessel. In the case of pulmonary embolisms, access may be gained through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible access and support catheters as possible.

The vasculature in the area in which the clot may be lodged is often fragile and delicate. For example neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

The clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore the inventors have discovered that the properties of the clot may be significantly changed by the action of the devices interacting with it. In particular compression of blood clot causes dehydration of the clot and results in a dramatic increase in both clot stiffness and coefficient of friction.

The clots may not only range in shape and consistency, but also may vary greatly in length, even in any one given area of the anatomy. For example clots occluding the middle cerebral artery of an ischemic stroke patient may range from just a few millimeters to several centimeters in length.

Stent-like clot retrievers are being increasingly used to remove clot from cerebral vessels of acute stroke patients. These are self expanding devices, similar in appearance to a stent attached to the end of a long shaft, and are advanced through a microcatheter and deployed across clot obstructions in order to trap and retrieve them. They rely on a pinning mechanism to grab the clot by trapping the clot between the self-expanding stent-like body and the vessel wall. This approach has a number of disadvantages:

A stent-like clot retriever relies on its outward radial force (RF) to retain its grip on the clot. If the RF is too low the stent-like clot retriever will lose its grip on the clot, but if the RF is too high the stent-like clot retriever may damage the vessel wall and may require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle all clot types.

The stent-like clot retriever pinning mechanism tends to compress the trapped clot. This compressive force will tend to dehydrate the clot, which in turn tends to increase its coefficient of friction, making it more difficult to remove from the vessel.

Conventional Stent-like clot retriever designs do not retain their expanded shape very well when placed in tension in bends, due to the manner in which their strut elements are connected to one another. This can result in a loss of grip on a clot as the stent-like clot retriever is withdrawn proximally around a bend in a tortuous vessel, with the potential escape of the captured clot. This occurs because the struts of the stent-like clot retriever are placed in tension when it is retracted. This tension is due to friction between the device and the blood vessel, and is increased if an additional load is applied load such as that provided by a clot. In a bend the struts on the outside of the bend are placed in higher tension than those on the inside. In order to attain the lowest possible energy state the outside surface of the stent moves towards the inside surface of the bend, which reduces the tension in the struts, but also reduces the expanded diameter of the stent-like clot retriever.

Another disadvantage with this approach is that it relies on pinning the clot between the stent-like clot retriever and the vessel wall and thus may not restrain the clot effectively when passing a branch vessel or when passing into a vessel that is larger than the fully expanded diameter of the stent-like clot retriever.

Pinning the clot between the stent-like clot retriever and the vessel wall in order to remove it from the vessel also results in high shear forces against the side of the clot as it is removed, potentially releasing fragments of the clot. If these fragments are not retained by the device they may be released leading to further blockages in the distal vasculature.

A particular difficulty encountered when attempting to remove long clots is that conventional devices may be shorter than the clot itself. A device that is shorter than the clot is unlikely to be able to restore flow through the occluded area upon deployment, and thus the pressure gradient across the clot remains a significant impediment to its removal. Simply making such a device longer would likely render it difficult to track through tortuous anatomies and could be traumatic to the vasculature, taking more force to withdraw and potentially getting stuck and requiring surgery to remove.

For many reasons including some or all of the above limitations it is often necessary for a physician to make multiple passes with a clot retrieval device in order to fully remove an obstructive clot. However each time a clot retrieval device is withdrawn the access to the target site is lost. Thus it is necessary to re-advance a guidewire and microcatheter to access and re-cross the clot, and then remove the guidewire and advance the clot retrieval device through the microcatheter. Navigating the guidewire and microcatheter to the clot can take a considerable amount of time especially if the vessels are tortuous. This additional time and device manipulation all adds to the risks to which the patient is exposed.

The challenges described above need to be overcome for any device to provide a high level of success in removing clot, restoring flow and facilitating good patient outcomes. Existing devices do not adequately address these challenges.

STATEMENTS OF THE INVENTION

According to the invention there is provided a clot retrieval device for removing occlusive clot from a blood vessel, the device comprising:—
- an inner elongate body having a collapsed delivery configuration and an expanded deployed configuration;
- an outer elongate body at least partially overlying the inner elongate body;
- the outer elongate body being expandable to a radial extent which is greater than the radial extent of the inner body in the deployed configuration to define a clot reception space;
- wherein the outer elongate body comprises a distal end portion; and
- wherein the inner elongate body comprises a main body portion and a distal portion which extends in the deployed configuration towards the outer elongate body to a greater extent than the main body portion,
- the distal portion of the inner elongate member and the distal end portion of the outer elongate body together defining a three dimensional protective structure to substantially prevent distal egress of clot or clot fragments from the device.

In this aspect of the invention the embolization risk is reduced by providing a distal net or scaffolding zone across the vessel lumen towards the distal end of the device. This scaffolding in this case is appended to both the inner or outer member or to both members, and is three dimensional in that it has depth as well as surface area. Combining the scaffolding of both inner and outer members provides a more effective filter than utilizing one member alone. In some cases fibres or fine wires are utilised to provide added scaffolding with minimal impact on device profile or deliverability.

In one embodiment the distal portion of the inner elongate body comprises a plurality of struts which are configured in a volumetric pattern.

In one case the distal portion of the inner elongate body comprises a bulged or flared framework of struts.

In one embodiment the distal end portion of the outer elongate body comprises distal struts. In one case the distal struts of the distal end portion of the outer elongate member are configured in a generally conical shape.

In one embodiment at least some of the struts comprise an attachment point, such as an eyelet, for reception of a fibre. The protective structure may include a plurality of fibres providing a distal net.

In one embodiment the outer elongate body comprises a first monolithic structure.

In one embodiment the inner elongate body comprises a second monolithic structure.

In one case wherein the inner elongate body extends proximally of a proximal end of the outer elongate body.

In one embodiment the outer elongate body comprises a plurality of clot receiving openings and a plurality of clot engaging regions, and wherein the clot engaging regions are adapted, on engagement with clot, to urge clot towards the clot receiving openings and into the reception space between the outer elongate body and the inner elongate body.

The clot engaging regions of the outer elongate body comprises scaffolding openings, the clot receiving openings being substantially larger than the scaffolding openings.

In one embodiment the outer elongate body comprises at least two longitudinally spaced-apart segments. There may be at least one hinge is provided between the segments.

The disclosed designs overcome many of the disadvantages of existing mechanical thrombectomy solutions.

Various interchangeable terms are used herein to describe those portions of the invention that are configured to engage with the clot, being generally deployed within the clot and engaging with it. These terms include "clot engaging portion", "expandable member", "expandable body", "clot engaging element"; while the terms "elongate basket", "engaging basket" and "stent basket" may also be used to describe this portion of the device.

Designs are disclosed in which a clot engaging portion of the device is configured to be expanded within an occlusive clot in a blood vessel so that the expanding engager allows the clot to migrate into a reception space within the body of the engager as the engager expands. The engager is delivered through a catheter to the site of the occlusion and is positioned within the clot. The engager is expandable at the site of the occlusion and starts to compress the clot as it is expanded. The engager surface comprises inlet openings and the inlet openings allow the clot to 'escape' from compression by displacing a significant portion of the clot through the inlet openings in the wall of the engager. Because a significant portion of the clot is urged through the inlet openings in the engager this minimizes compression of the clot and hence minimizes the resultant increase in the clot coefficient of friction. This also reduces the radial force on the vessel in the region of the clot which means a lesser force is required to withdraw the captured clot, which in turn means less vessel trauma and less tension on the distal vascular bed. The device is configured such that the radial force of the device acts strongly at a small diameter to engage with and grip clot, but acts softly at a larger diameter to gently contact the vessel wall are also disclosed.

Designs with dual expandable members are disclosed whereby the device comprises a first inner expandable member and a second outer expandable member the inner member being arranged substantially within the lumen of the outer member. The properties of the inner and outer members may be tailored independently of each other. The inner member may have a very different radial force to the outer member. The inner member may have a very different level of porosity to the outer member. The inner member may have a fully expanded diameter that is very different to that of the outer member. The length of the inner member may be different to that of the outer member. The shape of the struts of the inner member may be different to the shape of the struts of the outer member. There may be a clearance between the inner member and the outer member in the expanded configuration. There may be a clearance between the inner member and the outer member in the collapsed configuration. One, or both or neither of the inner and outer members may have a seam which runs substantially longitudinally along at least a portion of the wall of the member. One, or both of the inner and outer members may comprise a laser cut member, a braided member, a knitted member, an extruded member, a pultruded member, One or both of the inner and outer members may be manufactured with a process involving a laser cutting step, a braiding step, a knitting step, an extrusion step, a pultrusion step, an electropolishing step, a heat treatment step. One or both of the inner and outer members may comprise a tapered section, a flared section, a closed end section or a closed mid section. One or both members may comprise a substantially tubular or cylindrical section.

These dual expandable member devices have a number of benefits. (1) The inner member can be configured to provide a strong opening force to create a lumen through the clot and restore flow immediately on deployment. This flow lumen reduces the pressure gradient across the clot, making it easier to remove the clot. (2) The diameter to which the inner member expands may be tailored so as to reduce the risk of a reperfusion injury. With this embodiment the inner member expands to a diameter that is significantly smaller than the diameter of the vessel immediately adjacent to and distal of the occlusion. This small diameter inner member creates a small flow lumen across the occlusion and restricts the initial blood flow to the affected portion of the brain. This restricted blood flow ensures that the pressure applied to blood vessels immediately after flow restoration is lower than normal and this reduces the risk of bleeding in the ischemic vascular bed. Full perfusion is subsequently restored by removing the device and the clot. (3) The inner member may be configured to expand to a lesser diameter than the outer basket and to a lesser diameter than any vessel in which it is to be deployed. This means that a strong radial force may be safely exerted on the clot to open up a flow lumen, but need not be exerted on the vessel. (4) The inner member can serve to scaffold the lumen created through the clot, preventing the liberation of emboli from the clot into the resultant fast flowing bloodstream. (5) The inner member may at least partially comprise a stent and can provide a strong grip on the clot for the critical initial step of disengaging the clot from the vessel, enabling the outer basket to be configured with a low radial force. (6) The outer member may be configured to have large inlet openings so as to urge clot across the wall of the outer. The inner member on the other hand may be configured to prevent distal migration or fragmentation or embolization of clot that traverses the wall of the outer member. By configuring the outer member so as to encourage clot to traverse the wall of the outer member the device can more effectively disengage clot from the wall of the vessel while the device is also effective at preventing loss of clot material with an inner member with a shape and substructure that provides scaffolding.

Designs are also disclosed which further reduce this embolization risk by providing a distal net or scaffolding zone across the vessel lumen towards the distal end of the device. This scaffolding may be appended to either the inner or outer member or to both members, and may be three dimensional in that it has depth as well as surface area. Combining the scaffolding of both inner and outer members may provide a more effective filter than utilizing one member alone. Designs are disclosed utilising fibres or fine wires to provide added scaffolding with minimal impact on device profile or deliverability.

Designs are disclosed of devices with long and highly flexible inner members which may extend significantly proximally of the outer member, enabling the device to be used to retrieve particularly long clots. The small diameter and flexible inner member expands to provide a flow lumen through the clot (reducing the pressure gradient and making the clot easier to remove) but does not expand to the diameter of the vessel in which it is deployed. Thus the resultant device can be delivered and retrieved more safely (at much lower forces) than a similar length device whose diameter was configured to engage with the vessel over its entire length.

Designs are also disclosed of clot retrieval structures from which portions can be detached and left in-situ as implants. This might be desirable as a bail-out option in the event that the device became lodged in place and the physician felt that the force required to retrieve device was too high to be safely applied. This might also be desirable in the event that the occlusion was thrombotic or atherosclerotic—in which case the outer member could be detached and left in place as a stent to maintain a flow lumen through the clot and scaffold the lesion. Detachable designs are disclosed in which the outer member can be detached from the inner member, and in which one or both ends of the outer member can be reconfigured to allow the outer member to expand to a generally tubular shape which can appose the lesion and/or vessel wall.

Various embodiments of the invention are described in more detail below. Within these descriptions various terms for each portion of the devices may be interchangeably used as discussed previously. Each of the described embodiments are followed by a list of further qualifications (preceded by the word "wherein") to describe even more detailed versions of the preceding headline embodiment. It is intended that any of these qualifications may be combined with any of the headline embodiments, but to maintain clarity and conciseness not all of the possible permutations have been listed.

In one embodiment of the invention the treatment apparatus comprises a clot retrieval device comprising:—an elongate member, and an expandable clot engaging element configured to extend across the clot in its expanded state, the expandable clot engaging element comprising a first monolithic structure and a second monolithic structure, the first monolithic structure encircling the second monolithic structure over at least a portion of its length, the second monolithic structure comprising a proximal section, an intermediate section and a distal section, the distal section comprising an expansion.

Some optional features of this embodiment include:—
wherein the first monolithic structure is configured to substantially encapsulate the second monolithic structure;
wherein the first monolithic structure comprises a proximal section, an intermediate section and a distal section, the distal section comprising an enclosed distal end;
wherein the distal end of the clot engaging element comprises an enclosed distal end said enclosed distal end configured to capture clot fragments and/or to prevent distal migration of clot fragments;
wherein the expansion is configured to prevent clot fragment migration;
wherein the distal end of the first monolithic structure comprises an enclosed distal end said enclosed distal end defining a surface the surface configured as a clot fragment barrier surface;
wherein the clot fragment barrier surface comprises an interconnected network of struts;
wherein the distal section of the clot engaging element is configured to provide a three dimensional barrier to clot migration;
wherein the device further comprises a elongate connector element said elongate connector element comprising a proximal end and a distal end, the proximal end connected to the second monolithic structure and the distal end connected to the first monolithic structure;
wherein the elongate connector element comprises a spring element and said spring element is integral with the second monolithic structure;
wherein the first monolithic structure and the second monolithic structure are connected at their distal ends;
wherein the first monolithic structure and the second monolithic structure are not connected at their distal ends; and/or
wherein the proximal sections of said first and second monolithic structures are connected to a distal end of the elongate member.

In another embodiment of the invention the treatment apparatus comprises a clot retrieval device comprising:—an elongate member, and an expandable clot engaging element configured to extend across the clot in its expanded state, the expandable clot engagement element comprising a proximal segment, a clot engaging segment and a distal segment, the proximal segment configured to extend proximal of the clot in use and the distal end configured to extend distal of the clot in use, the clot engaging segment configured to engage with the clot in its expanded state, the distal end comprising a fragment protection structure, the fragment protection structure comprising a plurality of struts configured in a volumetric pattern.

Some optional features of this embodiment include:—
wherein the volumetric pattern comprises at least partially a conically shaped volumetric pattern;
wherein the volumetric pattern comprises at least partially a cylindrical volumetric pattern;
wherein the volumetric pattern comprises at least one plurality of interconnected struts;
wherein the volumetric pattern comprises at least two pluralities of interconnected struts;
wherein the volumetric pattern comprises a first plurality of struts arranged about a first axis and a second plurality of struts arranged about a second axis;
wherein the position of the first axis is moveable relative to the position of the second axis;
wherein the first axis and the second axis comprise centre lines and in use said centre lines may comprise straight and/or curved centre lines;
wherein the centrelines are deflectable relative to one another;
wherein the volumetric pattern comprises a terminal end;
wherein the terminal end comprises a terminal junction for at least some of said plurality of struts;
wherein the terminal end comprises a connection point at which said plurality of struts are terminated and/or connected;
wherein the volumetric pattern comprises a first plurality of struts, and a second plurality of struts;
wherein the second plurality of struts is at least partially encompassed by the first plurality of struts;
wherein the second plurality of struts encircles the first plurality of struts;
wherein the first plurality of struts is arranged about a first axis and the second plurality of struts is arranged about a second axis and said first and second axes are substantially parallel;
wherein the first plurality of struts is arranged about a first axis and the second plurality of struts is arranged about a second axis and said first and second axes are substantially parallel;
wherein the first plurality of struts comprises a conical shape; and or
wherein the second plurality of struts comprises a spherical shape, a flattened spherical shape, a cylindrical shape or a spindle torus shape.

In another embodiment of the invention the treatment apparatus comprises a clot retrieval device comprising:—an elongate member, and an expandable clot engaging element comprising a first tubular structure and a second tubular structure, the first tubular structure at least partially encircling the second tubular structure, the first tubular structure comprising a proximal end, a distal end, a proximal termination and a distal termination, the second tubular structure comprising a proximal end, a distal end, a proximal termination and a distal termination, the proximal termination of the first and second tubular structures being connected to the elongate member and the distal terminations of the first and second tubular structures being connected to each other.

Some optional features of this embodiment include:—
wherein the first tubular structure and the second tubular structure comprise monolithic structures of interconnected struts;
wherein the first tubular structure and the second tubular structure comprise longitudinally extending structures;
wherein both the first tubular structure and the second tubular structure comprise collapsed delivery configurations and expanded deployed configurations and the first tubular structure at least partially encircling the second tubular structure in both the expanded configurations and the collapsed configurations;
wherein one or both of the first tubular structure and the second tubular structure comprise a proximal collar for connecting one or both of the first tubular structure and the second tubular structure to a distal end of the elongate member;
wherein the at least one proximal collar comprises a partial collar; and/or
wherein the at least one proximal collar is cut from a hypotube and encircles at least a portion of a distal end of the elongate member.

In another embodiment of the invention the treatment apparatus comprises a clot retrieval device comprising:—an elongate member, and an expandable clot engaging element comprising a first tubular structure and a second tubular structure, the first tubular structure at least partially encircling the second tubular structure, the first tubular structure and the second tubular structure connected to a distal end of the elongate member at a connection point, the first tubular structure comprising a first proximal connecting strut and a first connector element, the second tubular structure comprising a second proximal connecting strut and a second connector element, the first connector element encircling the second connector element at the connection point.

Some optional features of this embodiment include:—
wherein the first connector comprises a collar;
wherein the second connector comprises a collar or partial collar; and/or
wherein the elongate member comprises a distal safety stop configured to prevent distal movement of the first connector and/or the second connector.

In another embodiment of the invention the treatment apparatus comprises a clot retrieval device comprising:—an elongate member, and an expandable clot engaging element configured to extend across the clot in its expanded state, the expandable clot engagement element comprising a first luminal structure and a second luminal structure, the first luminal structure being larger in diameter than said second luminal structure, the distal end of said first luminal structure comprising a plurality of struts converging towards the axis of the first luminal structure, the distal end of said second luminal structure comprising a plurality of struts diverging away from the axis of said second luminal structure.

Some optional features of this embodiment include:—
wherein the distal end of said first and second luminal structures are configured to form a three dimensional clot fragment migration barrier;
wherein the distal end of said second luminal structure further comprises an inflection region where a tangent to said plurality of struts is substantially parallel to the axis of said second luminal structure;
wherein the distal end of said second luminal structure further comprises a converging region where said plurality of struts converged on the axis of said second luminal structure;
wherein the distal end of said second luminal structure further comprises a second distal junction where said plurality of struts terminate;
wherein the distal end of said first luminal structure further comprises a first distal junction where said plurality of struts terminate;
wherein the first distal junction is distal of the second distal junction; and/or
wherein the first distal junction is connected to the second distal junction by a connector element.

In another embodiment of the invention the treatment apparatus comprises a clot retrieval device comprising:—an elongate member, and a clot engaging element comprising a collapsed delivery state and an expanded clot engaging state, the clot engaging element configured to extend across the clot in its expanded state, the clot engaging element comprising a proximal section, an intermediate section and a distal section, the intermediate section comprising a luminal structure and the distal section comprising an expansion region.

Some optional features of this embodiment include:—
wherein the diameter of the expansion region is larger than the diameter of the intermediate section in the expanded state;
wherein the clot engagement element comprising plurality of struts connected in a monolithic structure;
wherein the expansion region comprises a region of divergence and a region of convergence;
wherein the expansion region comprises an inflection point between the region of divergence and the region of convergence;
wherein the expansion region is integral with the intermediate section;
wherein the expansion region comprises a transition section the transition section comprising a plurality of struts connection the expansion region to the intermediate section;
wherein the expansion region comprises a tapering distal end;
wherein the device comprises an elongate member connected to the distal end of the expansion region; and/or
wherein in the expanded state the luminal structure is configured to define a flow lumen through the clot.

In another embodiment of the invention the treatment apparatus comprises a clot retrieval device comprising:—an elongate member, and a clot engaging element comprising a collapsed delivery state and an expanded clot engaging state, the clot engaging element configured to extend across the clot in its expanded state, the clot engaging element comprising a proximal section, an intermediate section and a distal section, the proximal section and the intermediate section comprising a luminal structure, the proximal section comprising a smaller diameter than the intermediate section.

Some optional features of this embodiment include:—
wherein the diameter of the proximal section is less than 60% of the diameter of the intermediate section;
wherein the diameter of the proximal section is less than 50% of the diameter of the intermediate section;
wherein the diameter of the proximal section is less than 40% of the diameter of the intermediate section;
wherein the diameter of the proximal section is less than 30% of the diameter of the intermediate section;
wherein the diameter of the proximal section is less than 25% of the diameter of the intermediate section;
wherein the diameter of the proximal section is less than 20% of the diameter of the intermediate section;
wherein the proximal section comprises a proximal axis and the distal section comprises a distal axis and the proximal axis is offset relative to the distal axis in the expanded state.
wherein the proximal section comprises a first sub-structure and the intermediate section comprises a second sub-structure;
wherein the luminal structure of proximal section extends through the luminal structure of the intermediate section;
wherein the luminal structure of proximal section interconnects with the luminal structure of the intermediate section;
wherein the clot engaging element comprises a transition section interspersed between proximal section and the intermediate section and configured to provide a smooth transition between the proximal section and the intermediate section; and/or
wherein the distal section comprises a plurality of struts configured in a closed distal end.

In another embodiment of the invention the treatment apparatus comprises a clot retrieval device comprising:—an elongate member, and an expandable clot engaging element configured to extend across the clot in its expanded state, the expandable clot engagement element comprising a first luminal structure and a second luminal structure, the first luminal structure being larger in diameter than said second luminal structure and encircling at least a portion of the second luminal structure, the second luminal structure extending substantially proximal of the first luminal structure.

Some optional features of this embodiment include:—
wherein the first luminal structure comprises a proximal section, an intermediate section and a distal section and the second luminal structure comprises a proximal section, an intermediate section and a distal section;
wherein the intermediate section of the second luminal structure extends substantially proximal of the intermediate section of the first luminal structure;
wherein the proximal section of the second luminal structure comprises a connection to a distal end of the elongate member;
wherein the proximal section of the first luminal structure comprises a connection to a distal end of the elongate member;
wherein the proximal section of the first luminal structure comprises a connection to the second luminal structure;
wherein the proximal section of the first luminal structure comprises a connector extending from the intermediate section to a connection point with the elongate member; and/or
wherein the connection point with the elongate member is proximal of the second luminal structure.

In another embodiment of the invention the treatment apparatus comprises a device for removing clot from a blood vessel comprising:—an elongate member, and an expandable clot engaging element configured to extend across the clot in its expanded state, the expandable clot engagement element comprising a first luminal structure and a second luminal structure, the first luminal structure being larger in diameter than said second luminal structure and encircling at least a portion of the second luminal structure, the second luminal structure comprising a clot capture structure at its distal end, the clot capture structure comprising a flared section.

Some optional features of this embodiment include:—
wherein the clot capture structure comprises a plurality of struts and at least one fibre configured into a filter;
wherein in the expanded state the diameter of at least a portion of the clot capture structure is similar to the diameter of the blood vessel;
wherein in the expanded state the diameter of at least a portion of the clot capture structure is larger than the diameter of the second luminal structure; and/or
wherein in the expanded state the diameter of at least a portion of the clot capture structure is similar to the diameter of the first luminal structure.

In another embodiment of the invention the treatment apparatus comprises a clot retrieval device comprising an elongate member, a first expandable member and a second expandable member; both expandable members having a proximal section, a body section, and a distal section, the body section of the first expandable member in the freely expanded state being larger in diameter than that of the second expandable member in the freely expanded state, and the proximal section of the first expandable member being distal of the proximal section of the second expandable member.

Some optional features of this embodiment include:—
wherein the distal section of the first expandable member comprises a clot capture structure;
wherein the distal section of the second expandable member comprises a clot capture structure;
wherein the clot capture structure comprises a plurality of struts;
wherein the clot capture structure comprises a plurality of struts and at least one fibre configured into a filter;
wherein the proximal end of the first expandable member is connected to the distal section of the elongate shaft;
wherein the proximal end of the first expandable member is connected to the second expandable member;
wherein the proximal end of the second expandable member is connected to the distal section of the elongate shaft;
wherein the distal end of the first expandable member is not connected to the distal end of the second expandable member;
wherein the distal end of the first expandable member is connected to the distal end of the second expandable member;
wherein the body section of the second expandable member in the freely expanded state is less than 50% of the diameter of the body section of the first expandable member in the freely expanded state;
wherein the body section of the second expandable member in the freely expanded state is less than 40% of the diameter of the body section of the first expandable member in the freely expanded state;
wherein the body section of the second expandable member in the freely expanded state is less than 30% of the diameter of the body section of the first expandable member in the freely expanded state; and/or
wherein the body section of the second expandable member in the freely expanded state is less than 20% of the diameter of the body section of the first expandable member in the freely expanded state.

A method of using a clot retrieval device to retrieve a clot from a vessel, said clot retrieval device comprising an expandable body and an elongate shaft, said method comprising: delivering the device through a microcatheter to a target site, retracting the microcatheter to deploy the device at least partially within or beneath the clot, expanding a proximal section of the expandable member within a proximal section of the clot to a diameter smaller than that of the vessel, expanding a distal section of the expandable member distal of the clot to a diameter substantially equal to that of the vessel, withdrawing the device and clot proximally and removing both from the patient.

Some optional features of this embodiment include:—
wherein the expandable body comprises an inner expandable member and an outer expandable member;
wherein the expanded diameter of the inner expandable member is smaller than that of the outer expandable member;
wherein at least a portion of the inner expandable member extends within at least a portion of the outer expandable member;
wherein at least a portion of the inner expandable member extends proximal of the outer expandable member;
wherein the distal section of the expandable body comprises a clot capture structure;

wherein the clot capture structure is connected to the inner expandable member;

wherein the clot capture structure is connected to the outer expandable member; and/or wherein the elongate shaft extends outside of the patient in use.

A clot retrieval device for removing occlusive clot from a blood vessel, the device comprising:—an elongate shaft; an inner elongate body having a collapsed delivery configuration and an expanded deployed configuration; an outer elongate body at least partially overlying the inner elongate body; the outer elongate body being expandable relative to the inner elongate body to a radial extent which is greater than the radial extent of the inner body in the deployed configuration; the proximal end of the outer elongate body being detachably fixed to the distal end of the elongate shaft.

Some optional features of this embodiment include:— wherein the proximal end of the outer elongate body comprises two or more struts;

wherein detachment of the proximal end of the outer elongate body from the distal end of the elongate shaft frees the proximal struts to expand apart;

wherein the outer elongate body adopts a substantially cylindrical or tubular shape upon detachment;

wherein the outer elongate body further comprises a closed distal clot capture structure comprising a plurality of struts converging at a terminal connection;

wherein the distal end of said plurality of struts are detachable from the terminal connection;

wherein detachment of said plurality of struts from the terminal connection frees the struts to expand apart;

wherein the device further comprises a detachment system; and/or wherein the detachment system comprises a pull-wire, a bio-absorbable collar or fibre, an electrolytic system or a resistance heating system.

BRIEF DESCRIPTION OF THE DRAWINGS

The invention will be more clearly understood from the following description of some embodiments thereof, given by way of example only, with reference to the accompanying drawings, in which:

FIG. 1a shows an isometric view of a clot retrieval device of this invention;

FIG. 1b shows a partially assembled isometric view of the proximal joint of the clot retrieval device of FIG. 1a;

FIG. 1c is an isometric view of the proximal joint of the clot retrieval device of FIG. 1a;

FIG. 1e is an end view of the clot retrieval device of FIG. 1a;

FIG. 1f is an isometric view of the distal end of the clot retrieval device of FIG. 1a;

FIG. 1g is a plan view of the outer member of the clot retrieval device of FIG. 1a;

FIG. 1h is a side view of the outer member of the clot retrieval device of FIG. 1a;

FIG. 1i is a side view of the inner member of the clot retrieval device of FIG. 1a;

FIG. 1j is an isometric view of the distal end of the inner member of the device of FIG. 1a;

FIGS. 2a to 2f show a method of use of a device of this invention;

FIG. 4b is a side view of the device of FIG. 4a;

FIG. 5a is an isometric view of a clot retrieval device of this invention;

FIG. 5b is an isometric view of a clot retrieval device of this invention;

FIG. 6 is an isometric view of a clot retrieval device of this invention;

FIGS. 7a to 7e show a method of use of a device of this invention;

FIG. 10a shows the distal end of a clot retrieval device of this invention;

FIG. 10b is an end view of the device of FIG. 10a;

FIG. 10c is a detail view of an attachment feature;

FIG. 11a shows the distal end of a part of a clot retrieval device of this invention;

FIG. 11b is an end view of the device of FIG. 11a;

FIG. 12 shows the distal end of a clot retrieval device of this invention;

FIG. 13a shows the distal end of a clot retrieval device of this invention;

FIG. 13b is an end view of the device of FIG. 13a;

FIGS. 15a to 15d show a method of use of a device of this invention;

FIG. 16 is an isometric view of the proximal joint of a clot retrieval device of this invention;

FIG. 17a is a side view of a clot retrieval device of this invention;

FIG. 17b is a detail view of a portion of the device of FIG. 17a;

FIG. 18 shows the distal end of a part of a clot retrieval device of this invention;

FIG. 19 shows a clot retrieval device of the invention partially restrained within a loading tool;

FIG. 20 shows a portion of a clot retrieval device of this invention;

FIG. 21a is a side view of a part of a clot retrieval device of this invention; and FIG. 21b shows a developed view of the part of FIG. 20a.

DETAILED DESCRIPTION

Figure 1D:
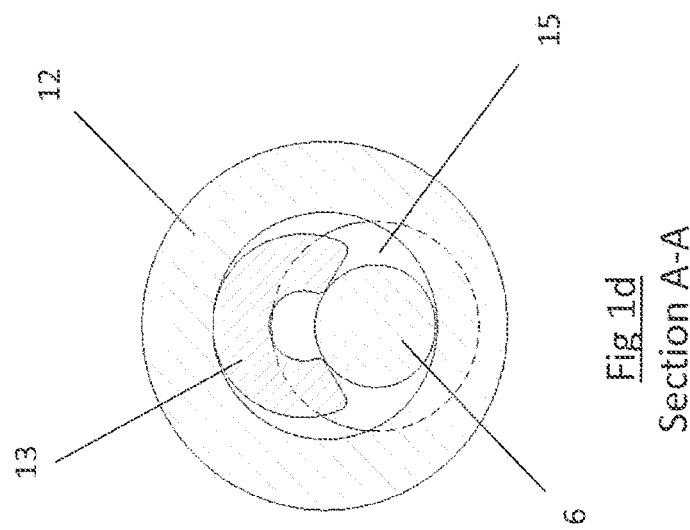
FIG. 1d is a section view through the device of FIG. 1c.

Specific embodiments of the present invention are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in cath lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in many cases in the context of treatment of intracranial arteries, the invention may also be used in other body passageways as previously described.

A common theme across many of the disclosed designs is a dual layer construction in which the device comprises an outer expandable member within which runs an inner expandable member, both members being directly or indirectly connected to an elongate shaft, and a distal net or scaffold configured at the distal end of the device to prevent the escape of clot fragments. This distal net may be appended to either the shaft, the inner or the outer members or to several of these. A range of designs are envisaged for each of these elements as described throughout this document, and it is intended that any of these elements could be used in conjunction with any other element, although to avoid repetition they are not shown in every possible combination. For example it is intended that the outer expandable member/outer cage of FIG. 1 could be used in conjunction with the inner expandable member of FIG. 4, or the distal net of FIG. 13 could be connected to the distal end of the inner expandable member of FIG. 5 in place of net 205 as shown.

Both the inner and outer expandable members are desirably made from a material capable of recovering its shape automatically once released from a highly strained delivery configuration. A superelastic material such as Nitinol or an alloy of similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of a huge range of shapes as disclosed herein and may be rendered visible under fluoroscopy through the addition of alloying elements (such as Platinum for example) or through a variety of other coatings or marker bands.

The inner expandable member may in some cases form a generally tubular structure and is ideally configured to expand to a lesser diameter than that of the smallest vessel in which it is intended to be used. This diameter is typically less than 50% that of the outer expandable member may be as low as 20% or less of the outer member diameter.

A range of different distal net or distal scaffolding zone designs are disclosed, some of which incorporate strut elements from the framework of the outer and/or inner expandable members, and some of which incorporate fine wires or fibres to provide added scaffolding with minimal impact of overall device profile or deliverability. Suitable materials ideally have a high tensile strength so that a very fine wire or fibre with sufficient integrity for manufacturability and use can be produced, such as for example polymers materials like UHMWPE, Aramid, LCP, PET or PEN, or metals such as Tungsten, MP35N, stainless steel or Nitinol.

FIG. 1a shows one embodiment of a clot retrieval device of the present invention. The clot retrieval device 1 has an elongate shaft 6 having a distal end that extends interior of the artery and a proximal end that extends exterior of the artery, a clot engaging portion configured at the distal end of the elongate shaft 6 having an outer expandable member 2 and an inner expandable member 3 to facilitate restoration of blood flow through clot immediately after the clot retrieval device 1 is deployed at an obstructive site. The outer member 2 and inner tubular member 3 comprises a collapsed configuration for delivery and an expanded configuration for clot retrieval, flow restoration and fragmentation protection. In one embodiment the inner expandable member comprises a generally tubular body section.

The inner and outer members are preferably made of a super-elastic or pseudo-elastic material such as Nitinol or another such alloy with a high recoverable strain. Shaft 6 may be a tapered wire shaft, and may be made of stainless steel, MP35N, Nitinol or other material of a suitably high modulus and tensile strength. Shaft 6 may have indicator bands 7 on the shaft to indicate to the user when the distal end of the device is approaching the end of the microcatheter during insertion. These bands are positioned so that as they approach the microcatheter hub or haemostasis valve they indicate the distal tip of the device is approaching the end of the microcatheter. These indicator bands can be formed by printing or removing or masking areas of shaft coating so that they are visually differentiated from the remainder of the shaft. In another embodiment the indicator bands 7 are recessed below the surface of the shaft to give tactile feedback to the user as they approach the microcatheter.

Shaft 6 has a coil 4 adjacent its distal end and proximal of the outer member 2 and inner tubular member 3. This coil 4 may be metallic and may be formed from stainless steel or from a more radiopaque material such as platinum or gold for example or an alloy of such a material. In another embodiment the coil 4 may be coated with a low friction material or have a polymeric jacket positioned on the outer surface of the coil. Adjacent to this coil 4 a sleeve 5 may be positioned on the shaft 6. This sleeve 5 may be polymeric and may be positioned over the tapered section of the shaft. The sleeve 5 may be rendered radiopaque through the addition of a filler material such as tungsten or barium sulphate. The sleeve 5 and shaft 6 may be coated with a material to reduce friction and thrombogenicity. The coating may consist of a polymer, a low friction lubricant such as silicon, a hydrophilic or a hydrophobic coating. This coating may also be applied to the outer member 2 and inner tubular member 3.

Figure 1B:
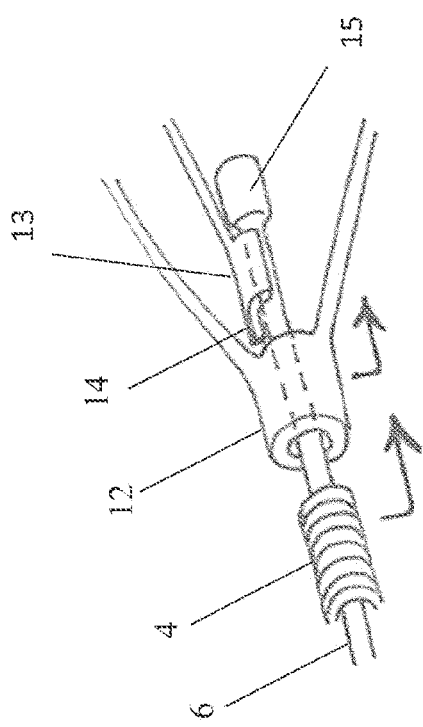
Figure 1C:
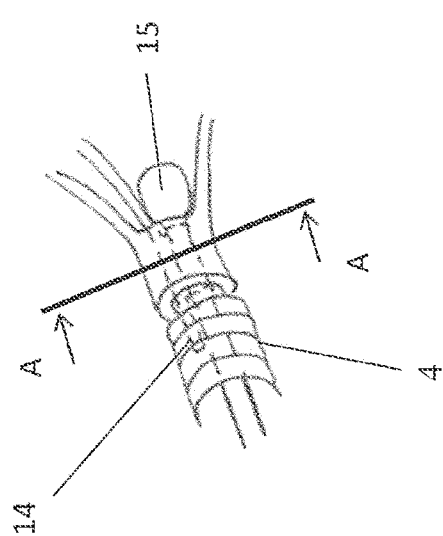

Referring especially to FIGS. 1b to 1d the shaft 6 may have integral collars or a step feature 15 to assist the integrity of the joints between the distal end of the shaft and the proximal ends of the inner tubular member 3 and the outer member 2. The proximal end of the outer member 2 may comprise of a collar 12 and the proximal end of the inner member 3 may comprise of a partial collar 13. The inner member partial collar 13 may be positioned on the shaft 6 proximal to the step feature 15 and the collar 12 of the outer member may be assembled over these features to form a mechanical lock to prevent joint disassembly under tension. FIGS. 1b and 1c show the assembly of this joint while FIG. 1d is a section view of the joint showing the mechanical lock. This lock is formed as the collar of the outer member 12 is eccentric to the shaft 6 and cannot slide over the step 15 of the shaft as long as the partial collar of the inner tubular member 13 is in position. Adhesive may be added to the assembled joint to further strengthen the joint and prevent disassembly under compression or other loading. In another embodiment a solder, weld or braze may be added to the assembled joint.

The collar of the outer member 12 is eccentric to the shaft 6 therefore in this embodiment a strut 14 is formed attached to the partial collar of the inner member 13. This strut 14 projects proximally and acts as a locating element for the proximal coil 4. When the proximal radiopaque coil 4 is located on the proximal strut 14 and the shaft 6, the coil is substantially concentric with the collar 12 of the outer member. Adhesive may be applied to the joint between the proximal coil and outer member collar to maintain the joint integrity. In another embodiment a solder, brazing or weld process may be used in this joint.

The outer member 2 is configured to self-expand upon release from a restraining sheath (such as a microcatheter) to a diameter larger than that of the inner tubular member 3. Expansion of the outer member 2 causes compression and/or displacement of the clot during expansion. When an expandable body provides a high level of scaffolding the clot is compressed. When an expandable body provides an escape path or opening the expanding body will urge the clot towards the opening. However if the expandable body provides only modest scaffolding the clot will be displaced but since the clot has many degrees of freedom it may move in a variety of different directions and therefore cannot be controlled. By providing a tubular expandable body where the length of the tubular expandable body is substantially as long as the length of the occlusive clot or longer, many of the degrees of movement freedom available to the clot are removed. When, as with the current invention, inlet openings 22 (as illustrated for example in FIG. 1g) are provided in the outer member 2 these inlets 22 provide the primary movement freedom available to the clot and so the expansion of the outer member 2 urges the clot into the reception space 11. The outer member 2 has multiple inlet mouths 22 to accept the clot. In this way inlet mouths 22 allow portions of the clot to enter reception space 11 of the outer member 2, and thus allow the clot to be retrieved without being excessively compressed. This is advantageous because we have discovered that compression of clot causes it to dehydrate, which in turn increases the frictional properties of the clot, and increases its stiffness, all of which makes the clot more difficult to disengage and remove from the vessel. This compression can be avoided if the clot migrates inward through the wall of the outer member 2 as the porous structure migrates outward towards the vessel wall.

FIG. 1g shows a plan view and FIG. 1h shows an elevation of the outer member 2. The inlet mouths 22 provide the added benefit of allowing the outer member 2 when retracted to apply a force to the clot in a direction substantially parallel to the direction in which the clot is to be pulled from the vessel (i.e. substantially parallel to the central axis of the vessel). This means that the outward radial force applied to the vasculature may be kept to a minimum, which in turn means that the action of the clot retrieval device 1 on the clot does not serve to increase the force required to dislodge the clot from the vessel, thus protecting delicate cerebral vessels from harmful radial and tensile forces.

Outer member 2 comprises proximal struts 20 connected at their proximal ends to a collar 12 and at their distal ends to a first expandable member 26. The proximal struts 20 may have a tapered profile to ensure a gradual stiffness transition from the shaft 6 to the clot engagement section of the device. The first expandable member 26 is connected to a second expandable member 27 by two connecting arms 29, which run from a proximal junction 39 to a distal junction 40. In one embodiment these connecting arms comprise generally straight struts running parallel to the central axis of the device. In other embodiments these connecting arms may comprise a plurality of struts configured in one or more cells, or may comprise curved or spiral arms. The region between the first and second expandable member comprises two inlet mouths 22 through which clot may pass and enter the reception space 11 defined by the region between the inner and outer members.

The second expandable member 27 is in turn connected to a third expandable member 28 by two connecting arms 30, which run from a proximal junction 41 to a distal junction 42. In one embodiment these connecting arms comprise generally straight struts running parallel to the central axis of the device. In other embodiments these connecting arms may comprise a plurality of struts configured in one or more cells, or may comprise curved or spiral arms. The region between the second and third expandable member comprises two inlet mouths 22 through which clot may pass and enter the reception space 11 defined by the region between the inner and outer members. The connecting arms between the first expandable member 26 and the second expandable member 27 may be substantially aligned with the connecting arms between the second and third expandable members 27,28 to align the neutral axis of the expandable members 26,27,28 during bending. In another embodiment the connecting arms between the first expandable member 26 and the second expandable member 27 may be aligned at an angle, such as 90° to the connecting arms between the second and third expandable members 27,28.

The first expandable member 26 comprises a series of interconnected struts, with certain struts such as strut 43 terminating in crowns with no distal connecting elements, and other struts such as 44 terminating in junction points such as 45 and 46. The second expandable member 27 comprises a series of interconnected struts, with certain struts such as strut 47 terminating in crowns with no distal connecting elements, and other struts such as 48 terminating in junction points. One or more expandable members may comprise marker bands or radiopaque features such as gold or platinum marker or coils. In this embodiment a gold oval marker 25 is shown fixed in an eyelet on a strut in the third expandable member 28. The gold marker is positioned to indicate to the user the distal end of the barrel section of the outer member to aid in accuracy of deployment. The struts in the expandable members may be configured so that during loading, multiple crowns do not align at the same distance from the proximal collar, for example 45 and 50. During loading or resheathing, a higher force is generally required to load a crown than a strut into the sheath, therefore if multiple crowns are loaded at the same time the user may notice an increase in loading force. By offsetting the crowns by making alternative struts 44 and 51 different lengths the loading force may be reduced and the perception to the user is improved.

The distal end of the third expandable member 24 comprises a circumferential ring of struts 23 connected to a series of struts 24 that ultimately terminate at a distal junction point 9, thus defining a closed end to the outer member. This series of struts may comprise a generally conical shape as shown in FIGS. 1a, 1f, 1g and 1h, or in other embodiments may comprise a generally flat plane which may be inclined or may be normal to the longitudinal axis of the device. In one embodiment (as shown) the distal junction point 9 comprises a collar. Struts 24 and 49 may be tapered to a narrower width than those of the more proximal struts comprising the body of the first and second expandable members, thus creating a gradual transition in the stiffness of the device both in the expanded and collapsed states.

Figure 1F:
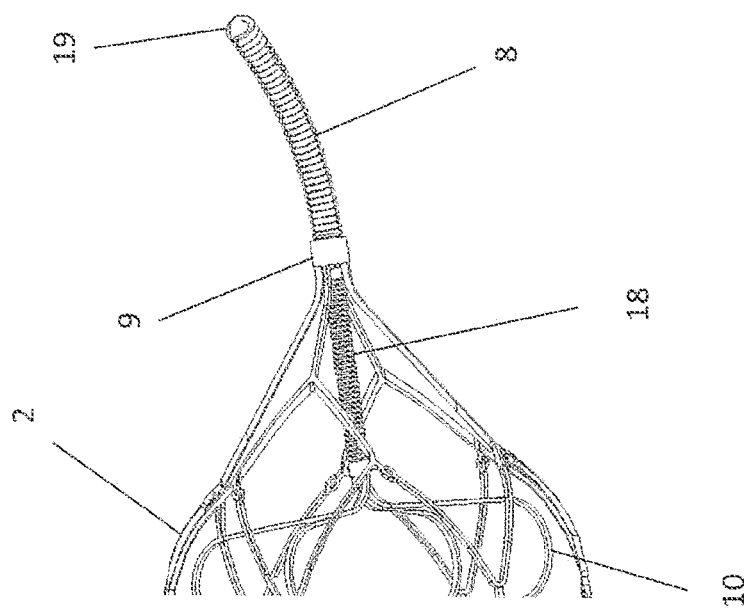
Figure 1E:
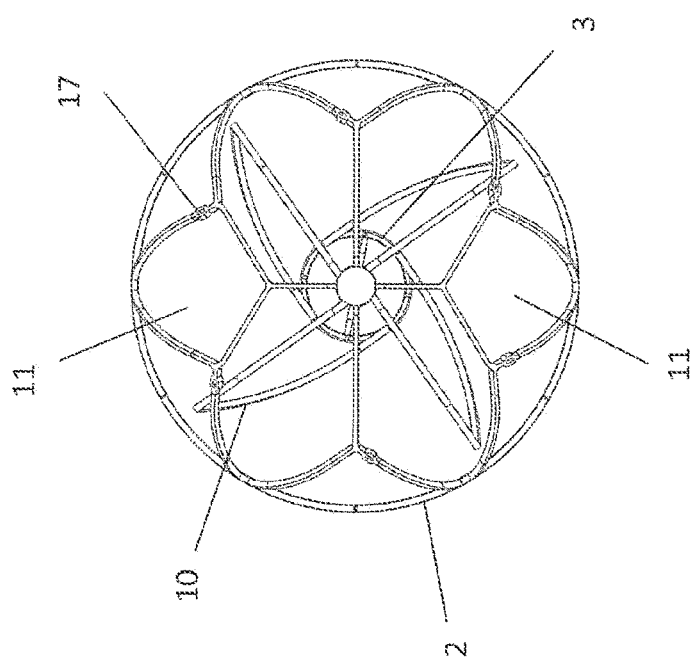

FIG. 1e shows the closed end of the outer expandable member 2 which prevents the egress of clot or clot fragments that have entered the reception space 11 between the inner and outer members. The expanded distal struts 10 of the inner member act as an additional three dimensional filter in combination with the closed distal end of the outer member 2 to further prevent the egress of clot or clot fragments. In certain embodiments this distal section may comprise fibre attachment points such as eyelets 17 or other fibre attachment features and fibres may be connected to the distal section at these attachment points to create a distal net.

FIGS. 1i and 1j show views of the inner tubular member 3. The inner tubular member 3 comprises a collapsed configuration for delivery and an expanded configuration for flow restoration and fragmentation protection. The inner tubular member 3 may comprise an elastic or super-elastic or shape-memory metallic structure and may further comprise a polished surface such as an electro-polished surface. The inner tubular member 3 is configured so as to provide a flow lumen through the device 1 to facilitate the immediate restoration of blood flow past the clot upon deployment. In one embodiment the inner tubular member 3 is configured to scaffold said flow lumen through the clot to prevent the liberation of fragments which might otherwise lodge in the distal vasculature. The inner tubular member 3 consists of a series of connected struts 31 that may contact a clot when initially deployed in a target vessel within the clot. The contact of the struts 31 of the inner tubular member 3 with the clot provides additional grip and assists in the initial dislodgement of the clot from the vessel when the device is retracted.

Inner tubular member 3 comprises a generally cylindrical section of interconnected struts 31, which is connected at its proximal end by strut 34 to partial collar 13. The distal end of the inner tubular member 3 consists of an expansile section formed from expanded struts 10 which have a diameter greater than that of the body section of the inner tubular member 3. These expanded struts are connected to a coil section 18 which in this embodiment is laser cut from the tubing that the inner tubular member 3 is also cut from during processing. The distal end of the coil 18 has a castellated profile 35 which is joined to the distal collar 9 of the outer member 2 during assembly. The distal end of the coil 18 on the inner tubular member 3 is bonded to the distal collar of the outer member 2 by adhesive. The castellated feature 35 on the inner tubular member 3 facilitates this adhesive bond and improves the strength of the bond by providing a reception space 38 for the adhesive within the collar and preventing it from wicking into the coil area. In another embodiment this joint may be assembled using a solder, weld or braze process.

The outer member 2 and the inner tubular member 3 are joined at the proximal and distal ends during assembly thereof to minimise tension within the members during use, the length of the outer member 2 should be substantially the same as the length of the inner tubular member 3 in the freely expanded configuration and the loaded configuration. The expanded struts 10 of the inner tubular member 3 elongate during loading so that the lengths of the inner and outer members are equal when fully loaded in a microcatheter. Length differentials between the inner tubular member 3 and the outer member 2 can still occur when the device is deployed in a small vessel or during the loading or deployment process. The coil 18 at the distal end of the inner tubular member 3 can accommodate minor length differentials by stretching without applying significant tensile or compressive forces to the device. In another embodiment this coil could be formed separately to the inner tubular member 3 and then be assembled to it. The coil could be formed from a stainless steel material, a polymer or from a more radiopaque metal such as gold or platinum or an alloy of such a material. The coil could also be replaced with a longitudinal length of an elastic material such as a low modulus polymer or elastomer.

FIG. 1f shows the distal end of the assembled device 1 and FIG. 1j shows the distal end of the inner tubular member 3. The distal end of the inner tubular member 3 also comprises a distal arm 32. The arm may be laser machined from the same tube as the rest of the inner tubular member. A radiopaque coil 8 (which may be platinum or gold or an alloy of same) is positioned over the distal arm 32 and butts against the distal collar 9 of the outer member 2, where it is connected by an adhesive joint to the collar 9 and arm 32. The distal tip of the arm 32 and the distal end of the radiopaque coil 8 are also connected by an adhesive joint. The distal arm 32 has a profile 37 at the distal tip which facilitates the adhesive joint by providing a reception space 36 for the adhesive within the radiopaque coil 8 and preventing the adhesive wicking up the coil. This adhesive joint forms a substrate for the application of additional adhesive to form a semi-spherical atraumatic tip 19 on the distal end of the device.

In other embodiments the inner tubular member may not be connected to the distal end of the outer member at all, or may be constrained within the outer member without being fixedly attached. In other embodiments the inner tubular member may have a non-cylindrical cross-section, may be non-uniform in diameter, and may have tailored strut patterns to provide regions of differing radial force or flexibility.

Figure 2D:
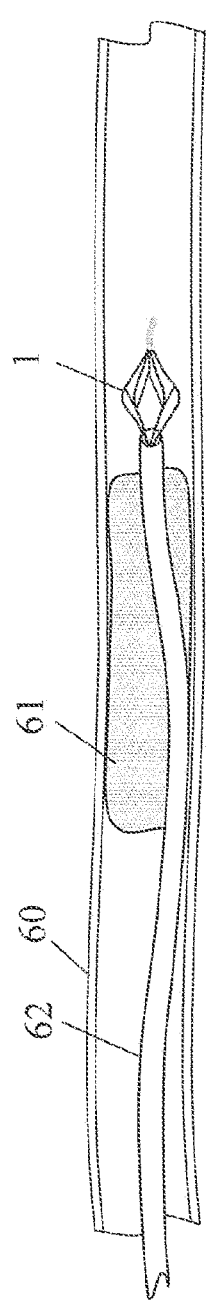
Figure 2E:
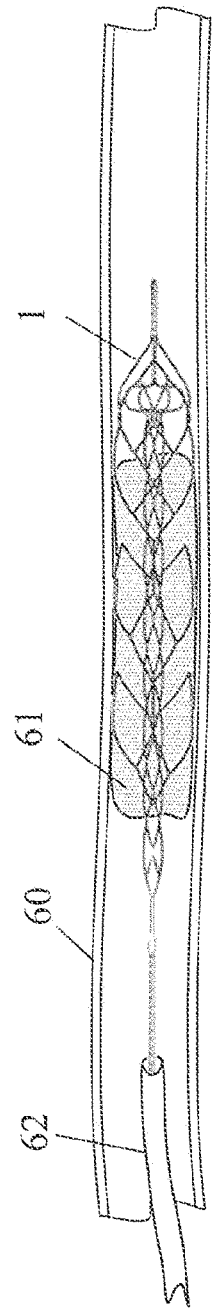
Figure 2F:
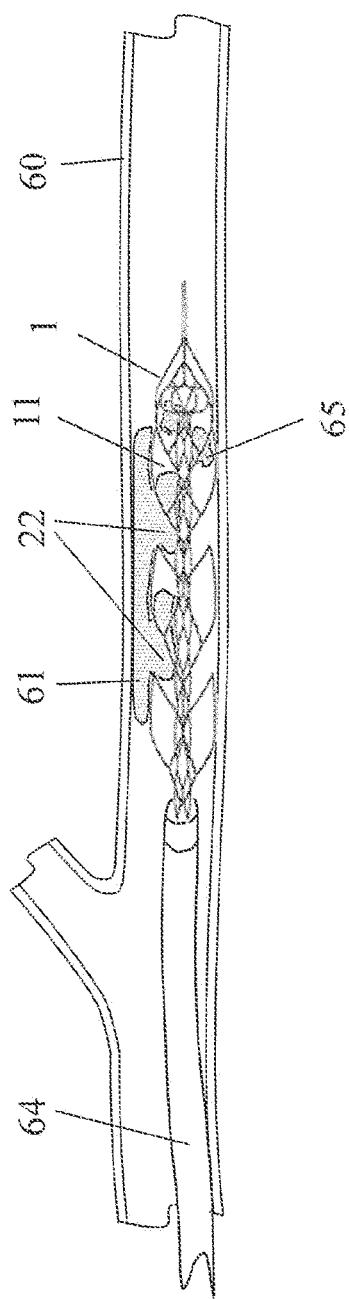

FIGS. 2a-2f shows a method of use of a device of this invention. A guidewire 63 and microcatheter 62 are inserted in the artery 60 and are advanced across the obstructive clot 61 using conventionally known techniques. When the microcatheter 62 is positioned distal to the occlusive clot 61, the guidewire 63 is removed from the artery 60 to allow the clot retrieval device 1 be advanced through the microcatheter 62. The device 1 is advanced in a collapsed configuration until the distal tip of the device 1 reaches the distal end of the microcatheter 62. The microcatheter 62 is retracted while the position of device 1 is maintained to deploy the clot retrieval device 1 across the clot 61 in a manner that the distal end of the device 1 is preferably positioned distal of the clot 61. The device 1 expands so that the outer member 2 engages with the occlusive clot and the inner tubular member 3 expands to engage the clot and provide a flow channel to restore blood flow in a controlled manner through the occlusive clot 61. The device 1 may be allowed to incubate for a period of time within the clot 61 if desired, as controlled flow has been restored through the inner tubular member 3. Retracting the device 1 dislodges the clot from its position in the artery 60 and further withdrawal of the device retrieves the clot 61 until it can be retrieved into the guide catheter 64 or introducer sheath. FIG. 2f illustrates the clot engaged with the device during retrieval into the guide catheter 64. The clot is partially located in the inlet openings 22 of the device 1 and also partially located in the reception space 11 defined by the region between the inner and outer members. Clot fragments 65 are shown trapped in the distal end of the device 1 where the closed end of the outer member and the expanded struts of the inner member have prevented the fragments from being released in the blood flow. Flow occlusion, aspiration and other standard techniques may be used during the clot retrieval process. The device 1 may be rinsed in saline and gently cleaned before reloading in the insertion tool. The device 1 may be reintroduced into the microcatheter to be redeployed in additional segments of occlusive clot, if required.

Figure 3B:
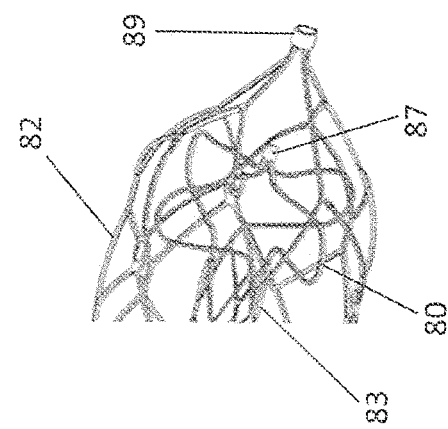
FIG. 3b shows the distal end of a clot retrieval device of this invention.
Figure 3A:
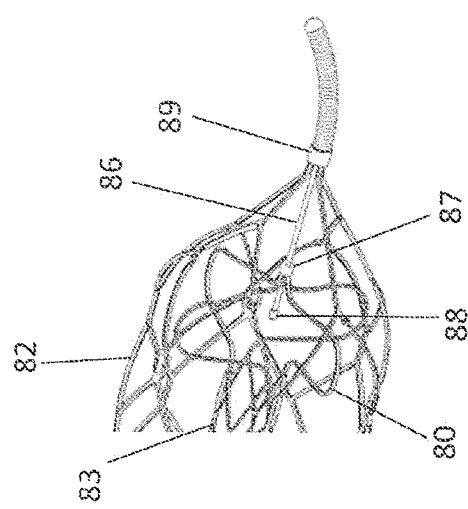
FIG. 3a shows the distal end of a clot retrieval device of this invention.

An isometric view of the distal end of another embodiment of a clot retrieval device similar to device 1 is shown in FIG. 3*a*. In this embodiment there is no fixed distal connection between the outer member 82 and the inner tubular member 83. The expanded struts 80 or the distal end of the body section of the inner tubular member 83 terminate at a collar 87 which can slide on a wire 86 to accommodate length differentials between the inner and outer members that occur during use when the device is expanded, collapsed or deployed in a small vessel. The wire 86 may be joined to the outer member 82 at the collar 89 by an adhesive, solder, weld or braze joint. The wire 86 comprises a step, collar or flare feature 88 which prevents the collar 87 of the inner tubular member 83 disengaging from the wire 86. The wire 86 may be metallic and be formed from stainless steel or Nitinol, alternatively it may be formed from a high durometer polymer such as PEEK or Polyimide or as a polymer jacketed metallic wire. The wire 86 may also be formed by laser cutting and be cut from the same tubing that the outer member 82 is processed from. In this case the wire 86 would be an integral part of the outer member 82 and be connected at the distal collar 89. To assemble the inner tubular member 83 and the wire 86, a slot may be cut in the collar 87 of the inner tubular member 83. The step 88 on the proximal end of the wire 86 may have a radiused atraumatic proximal end and may be connected by a fibre to another part of the device to minimise the degrees of freedom of the wire to prevent the proximal end of the wire protruding through the outer member 82 when the device is in a curved configuration. This fibre may be connected to a proximal collar of the inner or outer members and may be formed from an elastic material.

An isometric view of the distal end of another embodiment of a clot retrieval device similar to device 1 is shown in FIG. 3*b*. In this embodiment there is no distal connection between the distal ends of the inner 83 and outer expandable 82 members. In this embodiment the bulged or flared end 80 of the inner expandable member 83 acts as a guide to keep the inner member within the outer member. This embodiment differs from that of device 1 in that it has no distal tip—rather a rounded end 89 is positioned at the distal most point of the outer member to render it atraumatic to the vessels in which it is used. In other similar embodiments the inner member bulge or flared section 80 comprises struts configured in a spiral shape, or configured in cellular patterns so that the struts of the bulge or flare are not parallel to those of the adjacent portion of the outer member. Ideally the struts of the bulge or flare are perpendicular, or closer to perpendicular than parallel to those of the adjacent portion of the outer member. In this way the bulge or flare will be prevented from moving outside the outer member when the device is positioned in bends.

Figure 4A:
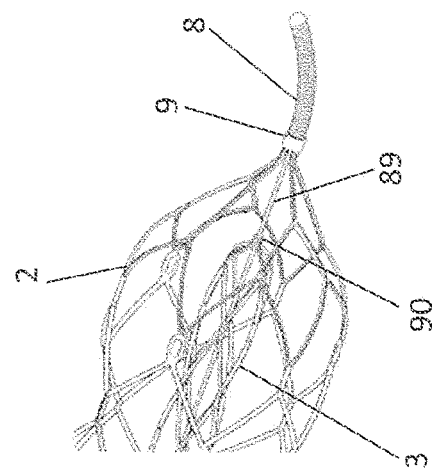
FIG. 4a is an isometric view of the distal end of a clot retrieval device of this invention.
Figure 4B:
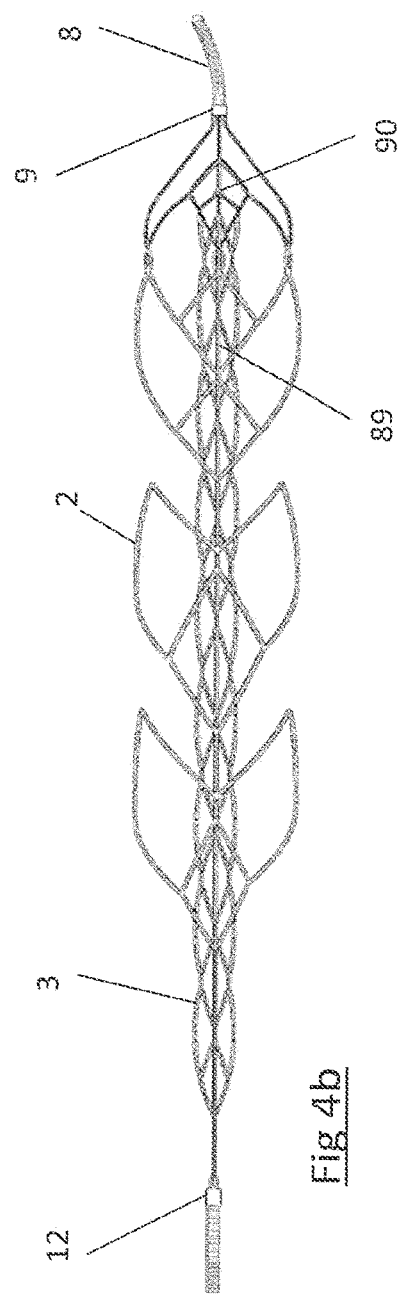

Another embodiment of the device is shown in FIGS. 4*a* and 4*b*, where FIG. 4*b* is a side view of the device and FIG. 4*a* is an isometric view of the distal end of the same embodiment. In this embodiment an elastic fibre 89 may be connected to the proximal collar 12 of the outer member 2 or the proximal end of the inner tubular member, and to the distal collar 9 of the outer member 2. This fibre 89 is positioned inside the inner diameter of distal collar 90 of the inner member 3 and facilitates the collar 90 sliding proximally or distally on the elastic fibre 89. Therefore as the length differential between outer member 2 and inner member 3 changes during use when the device is expanded, collapsed or deployed in a small vessel, the fibre 89 can elongate or contract as necessary to maintain the collar 90 of the inner member 3 in a generally central location in the outer member 2. The fibre may be formed from a low durometer polymer material, a rubber or elastomer or be a combination of a high durometer fibre and a small diameter coil spring. The coil spring could be formed from a metallic material or a polymer or a combination of both such as a polymer jacketed wire.

Referring now to FIG. 5*a*, there is shown a clot retrieval device 150 comprising an elongate shaft 151, an inner expandable member 153, and an outer expandable member 154. The outer expandable member comprises a plurality of struts 158 and connecting elements 157, and further comprises a distal scaffolding zone 155 and a distal tip 156. In the embodiment shown the outer expandable member is connected to the inner expandable member by connecting arms 159 at connecting junctions 160. In another embodiment the shaft 151 may extend through the inner expandable member and the outer expandable member may be connected to a distal region of said shaft. In yet another embodiment the portion of the inner expandable member proximal to the outer expandable member may be formed from the same piece of material (for example a single piece of nitinol tubing) as the outer expandable member, and the portion of the inner expandable member distal to the proximal end of the outer expandable member may be formed from a separate piece of material. The inner expandable member is connected to shaft 151 at connection point 152. The proximal end of the elongate shaft is configured to extend outside of the patient so that the user can use it to control the clot retrieval device position within the patient.

Each of the shaft and inner and outer expandable members may be constructed in a variety of manners as disclosed herein. This dual layer construction is intended to allow clot to enter through the large openings 161 of the outer expandable member and sit in the reception space 162 provided between the two expandable members. The inner member has a denser scaffold than that of the outer such that the clot is prevented from entering its lumen, thus creating a flow channel across the clot once the device is deployed across it. The long proximal portion of the inner member can be constructed with a very small volume of material, as it only expands to a fraction of the diameter of the outer member, and can thus be highly flexible in both the collapsed and expanded states. A significant benefit of this proximally extending member is that it allows a flow channel to be created across very long clots without overly compressing the clot or engaging with the vessel wall.

The distal scaffolding zone may comprise a generally conical tapering of the distal end of the outer member defined by a plurality of strut elements. In one embodiment one or more fibres are attached to the distal region of the outer member to increase the scaffolding by reducing the pore size of the openings in a manner similar to that shown in FIG. 12. In another embodiment the outer member may terminate more abruptly in a manner similar to that shown in FIG. 10*a*, in which design fibres or wires may be connected to the outer member to span its distal end and create a fragment capture zone. These fibres or wires may also be connected to the inner member, or indeed in yet another embodiment similar to that shown in FIG. 5*b* the distal scaffolding zone or distal net may be connected only to the inner member.

FIG. 5*b* shows another clot retrieval device 200 of this invention similar to device 150 of FIG. 5*a* but in which the distal net or scaffolding zone is attached to the inner expandable member rather than the outer, and in which the outer expandable member is attached to the shaft 201 rather than to the inner member. The inner expandable member 203 is attached to elongate shaft 201 at connection 202. This connection may comprise a collar. The outer expandable member 204 is connected by connecting arms 206 to the distal segment 207 of shaft 201 at point 209. Radiopaque markers 208 are attached to the distal end of outer member 204. A distal net 205 is attached to the distal end of the inner member 203.

The outer expandable member 204 comprises clot scaffolding regions 210 and inlet openings 211 such that clot is urged by the scaffolding regions to flow through the openings into the reception space 212 between inner and outer members as described in more detail elsewhere.

In other embodiments the inner and outer members and distal net may comprise any of the designs disclosed elsewhere herein for these elements. In this embodiment connecting arms 206 of the outer member pass through openings in the framework of inner member 203 and join to the shaft, while in other embodiments the outer member may be attached directly to the inner member. In yet another embodiment the portion of the inner expandable member proximal to the outer expandable member may be formed from the same piece of material (for example a single piece of nitinol tubing) as the outer expandable member, and the portion of the inner expandable member distal to the proximal end of the outer expandable member may be formed from a separate piece of material.

FIG. 6 shows another clot retrieval device 250 of this invention in which the inner expandable member and the outer expandable member do not overlap and are formed into a continuous framework which could be made from a single piece of material in a monolithic structure. The expandable body 257 comprises a proximal portion 252 which is smaller in expanded diameter than distal section 253, such that distal section 253 may be configured to engage with the wall of the vessel in which the device is intended to be used, while proximal section 253 may be configured to expand to a diameter smaller than said vessel, such that proximal and distal portions perform somewhat in the manner of the previously described inner and outer members. Proximal portion 252 of expandable body 257 is attached to the distal portion of elongate shaft 251. The distal struts 255 of the expandable body may in other embodiments be terminated in a conical scaffolding region similar to that shown in FIG. 1a, or may be attached to a distal net such as for example that shown in FIG. 4.

FIGS. 7a-7e show a method of use of a device of this invention. For illustration, the device 200 of FIG. 5 is shown being used to retrieve a long occlusive clot 301 from vessel 300. In the case of an intracranial occlusion a variety of access routes are possible, including a direct stick into the carotid artery, a brachial approach, or a femoral access. Once access has been gained to the arterial system using conventional and well understood techniques, a guide catheter or long sheath 307 (not shown in FIGS. 7a-d) is typically placed as close to the occlusive clot as practical. In the case of a middle cerebral artery occlusion the guide catheter might be placed in the internal carotid artery proximal of the carotid siphon. A microcatheter 302 is then advanced across clot 301 with the aid of a guidewire 303. In some cases an additional catheter (which may be known as a Distal Access Catheter or DAC) may be used in a triaxial system such that the microcatheter is advanced through the DAC, which is in turn advanced through the guide catheter or long sheath.

Once the microcatheter tip has been advanced across and distal of the clot the guidewire is removed and the clot retrieval device 200 is advanced through the microcatheter until it reaches its distal end as shown in FIG. 7c. The microcatheter is then retracted, allowing the clot retrieval device 200 to expand within and either side of the clot as shown in FIG. 7d. Because the device is configured with a long inner expandable member 203, this member can extend proximal of even a very long clot and upon device deployment the expansion of this member creates a flow channel through the clot, restoring flow to the vascular bed distal of the clot and reducing the pressure gradient across the clot. This reduction in pressure gradient reduces the force required to disengage the clot from the vessel wall and retract it proximally. The scaffolding regions 210 of the outer expandable member 204 expand within the distal portion of the clot applying a compressive force to discrete regions of the clot, thus urging the clot to flow away from these regions, through the inlet openings 211 and into the reception space 212 between the inner and outer members. This causes compression in discrete regions 304 of the clot, but causes minimal compression in regions 305 of the clot, or in the region proximal of the outer member. Minimizing compression on the clot in this way minimizes the forces applied radially outward to the vessel wall, which in turn reduces the frictional force to be overcome when retracting the clot. Because the inner member has created a channel through which blood can pass to the distal vascular bed, the device can be safely left in place for a dwell period prior to withdrawal. This dwell period is desirably greater than one minute and may be as long as 30 minutes or more. Allowing the device to sit in this way allows the clot to flow into the device which facilitates gripping it securely for retrieval. It also allows the distal vascular bed to be gently perfused with fresh oxygenated blood rather than be exposed to a sudden jump in pressure and flow as would be the case if the clot were immediately removed or if the device were to compress the clot so much that a very large flow channel was created upon deployment. Once the dwell period has elapsed the device and microcatheter (not shown) can be retracted back into either the DAC or guide/sheath as shown in FIG. 7e. This may be done with the aid of aspiration through the guide/sheath or DAC to assist in retaining a firm grip on the clot and avoiding fragment loss, however the disclosed designs which grip the clot securely and house the clot safely within a reception space and further comprise a distal net or scaffolding region have the advantage that they can be safely used without aspiration. The distal net 211 may be spaced apart from the distal end of the outer member as shown such that it is optimally positioned to trap any fragments released from the clot during retraction even if these fragments originate from that portion of the clot not fully housed with reception space 212. Such a fragment 308 is shown in FIG. 7e.

Figure 8:
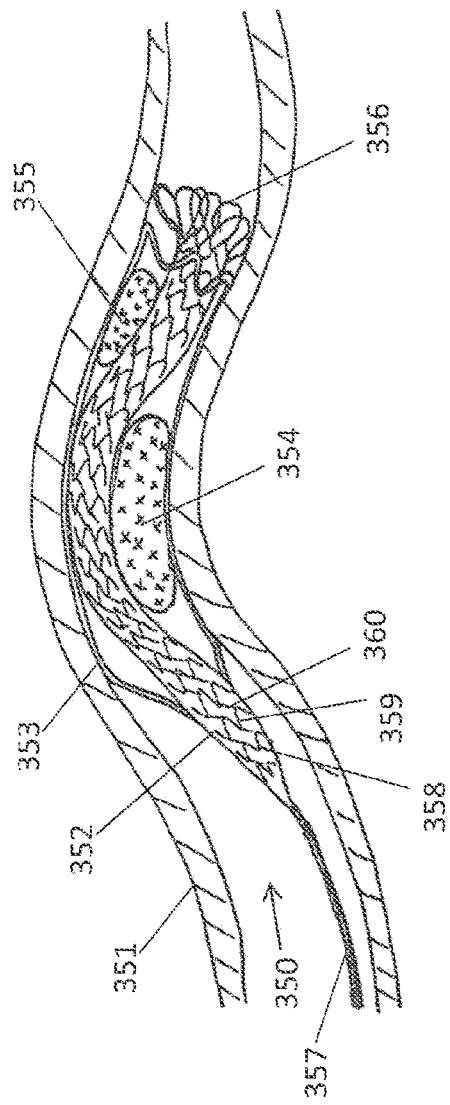
FIG. 8 shows a clot retrieval device deployed within a clot in a vessel.

FIG. 8 shows another clot retrieval device 350 of this invention in which the inner expandable member 352 is designed to be particularly flexible. The device comprises an inner expandable member 352, an outer expandable member 353, a distal protection net 356 and an elongate shaft 357. The inner and outer expandable members are attached to a distal section of the shaft, and the distal protection net is attached to the end of the inner expandable member. The device is shown deployed in a vessel 351 within a clot 354 and 355. The compliant inner member is displaced in one direction by one portion 354 of the clot, and in a different direction by a second portion 355 of the clot.

In the embodiment shown the compliance of the inner member is made possible by the design of the framework of struts and connectors from which this member is formed. The inner member illustrated in FIG. 8 comprises a series of generally cylindrical rings 358 formed by struts 359 and connected to an adjacent ring by connectors 360. In order to optimize the clot scaffolding properties of the member all of the crowns of each ring 359 are connected to another crown by a connector 360, thus creating a dense, closed cell structure. However such a structure is generally less flexible than an open cell structure in which not all crowns are connected. This problem is overcome by inclining the connectors at an angle to the axis of the inner member so that when the member is placed in a bend the resultant load on the connectors is a flexural load rather an axial compressive or tensile load. For a given bend angle this flexural load can be accommodated at a much lower strain level than would be possible were the connector aligned with the axis of the member, therefore the resultant inner member can be flexed and bent much more easily than would be the case with conventional axially aligned connectors.

In yet another embodiment the inner member is constructed in a similar fashion to that described above except that the connectors alternate in direction between each adjacent ring—for example all of the connectors between the first and second rings may be oriented clockwise, while all of the connectors between the second and third rings may be oriented anticlockwise. Thus when the device expands or contracts each ring twists relative to its adjacent ring, but each twist counterbalance the next so that minimal twisting occurs to the distal end of the inner member relative to the proximal end.

In yet another embodiment the inner member comprises a closed cell pattern of cells, each cell bounded by struts, and the cells configured in a generally spiral pattern around the circumference of the member.

In another embodiment the inner member comprises a braided structure, formed from one or more wires. The braided structure comprises a series of opposing spirals, with multiple overlap points where one wire crosses over another. At least some of these crossover points are not fixed attachment points, so that the member can easily accommodate a bend by a sliding action of one wire over another at these crossovers.

In yet another embodiment the inner member comprises an open cell framework of struts and connectors.

Figure 9:
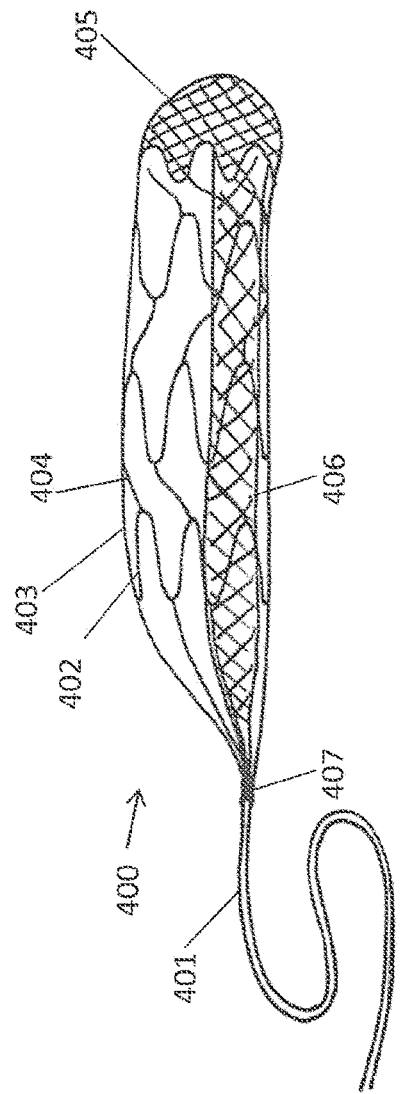
FIG. 9 is a side view of a clot retrieval device of this invention.

FIG. 9 shows another clot retrieval device 400 of this invention in which the inner expandable member 406 is offset relative to the outer expandable member 403. Such a construction may be desirable for several reasons. One such reason is to aid manufacturability in the event that the outer member is formed from a large diameter tube or from a flat sheet and thus has a proximal end or apex 407 that is offset from the centreline of the outer member and is in or close to the cylindrical plane defined by the outer surface of the member. In the embodiment shown the inner member 406 and outer member 403 are connected at their proximal ends to the distal end of shaft 401 at connection point 407, which is offset from the central axis of the expanded outer member, and hence of the vessel in which the device is intended to be deployed. A distal net 405 is appended to the distal end of the outer member 403.

FIGS. 10a (side view) and 10b (end view) show the distal region of another clot retrieval device 450 of this invention in which a distal fragment protection feature is created by the attachment of shaped wires or fibres 455 between eyelets 453 on crowns 456 of outer member 452 and eyelets 454 on crowns 457 of inner member 451. The shaped wires or fibres may be formed in a variety of shapes to optimize the coverage of the aperture at the end of the device. In the embodiment shown the shape is generally two dimensional sinusoidal pattern. In another embodiment the shape may three dimensional and more similar to that shown in FIG. 12. The wires or fibres may be made from polymer materials like UHMWPE, Aramid, LCP, PET or PEN, or metals such as Tungsten, MP35N, stainless steel or Nitinol. An advantage of using Nitinol or a similar shape memory material is that the wire can recover to its formed "memorized" shape upon deployment. The wires or fibres may in other embodiments be attached to features on the framework of the inner or outer members other than eyelets in the crowns, or may be simply passed through cells of either member to create an attachment location.

FIG. 10c depicts an alternative connection hook 477 design that could be incorporated in a strut 475 of an inner or outer expandable member to permit the attachment of a wire or fibre without needing to thread an end of the wire or fibre through an eyelet. Instead the wire or fibre may be slotted into place. The recesses created by lips 476 and 478 aid in retaining the wires or fibres in position.

FIGS. 11a (side view) and 11b (end view) show the distal region of another clot retrieval device 500 of this invention in which a three dimensional distal fragment protection feature is created by a bulged framework of struts. Expandable member 501 comprises multiple crowns 504, to which are connected a plurality of filter arms 502, which terminate at connection point 503. The filter arms are flared radially outward to form a bulged shape of a larger diameter than the body of the expandable member 501, which might in some embodiments be the inner expandable member of a clot retrieval device. The flared filter arms 502 are also spiraled so that in end view they cross over one another at least at points 505 as shown in FIG. 11b. This spiraling serves to reduce the area of the openings 506 through which fragments of clot might otherwise escape. In another embodiment the filter arms are not spiraled. In yet another embodiment the filter arms originate from crowns which are themselves expanded to the diameter of the bulge. In yet another embodiment the enclosed space 507 formed beneath the bulge of the filter arms is filled with a second material. In one embodiment this second material comprises a filter mesh, which may be formed of one or more lengths of wire of a material such as Nitinol, similar to the design shown in FIGS. 13a and 13b.

FIG. 12 shows the distal region of another clot retrieval device 550 of this invention in which an inner expandable member incorporating a three dimensional distal fragment protection feature 500 (previously shown and described) is contained within an outer expandable member 551 comprising a conical tapering distal end 552. The resultant structure provides multiple layers of fragmentation protection and is particularly affective at dealing with large fragments and large volumes of fragments without the fragments gathering together in one point and causing an obstruction to flow through the device. The distal conical section of the outer expandable member 551 comprises a plurality of struts 552, which in turn comprise a plurality of eyelets 554, through which are threaded one or more fibres 555 to create a scaffolding net across the lumen of the vessel in which the device is deployed.

Figures 13A, 13B:
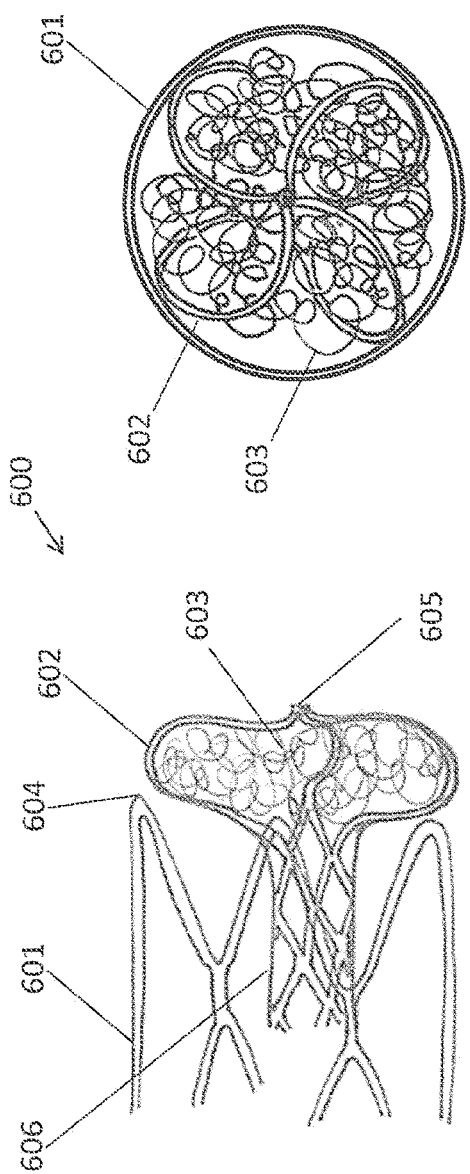

FIGS. 13a (side view) and 13b (end view) show the distal region of another clot retrieval device 600 of this invention. The device comprises an outer expandable member 601 and an inner expandable member 606. The inner expandable member 606 incorporates a bulged or flared distal section 602, similar to that of part 500, within which is retained a mesh-like structure 603 formed from wire or fibre. In one embodiment the opening angles of the cells of the inner and outer expandable members are configured such that the outer member foreshortens to a greater degree than the inner member upon expansion, with the result that the bulged filter section 602 is situated beneath or proximal to distal crown 604 of the outer member when in the collapsed/wrapped down configuration for delivery, but is situated distal to crown 604 when in the expanded configuration. This change in relative positions is advantageous to minimize device length and parking space during delivery and deployment, and to maximise the effectiveness of the fragment protecting filter during retrieval. In one embodiment the mesh-like structure 603 is formed from randomly curled fine wire, where this wire is preferably Nitinol wire, and is preferably of less than 50 microns in diameter, and most preferably less than 25 microns in diameter. In another embodiment the mesh-like structure 603 is formed from a polymer fibre, where this fibre is preferably an Aramid, LCP, UHMWPE, PET or PEN and is preferably of less than 50 microns in diameter, and most preferably less than 25 microns in diameter. The fibres or wire may be randomly curled and/or twisted to occupy the space within the bulge, or they may be shaped into a specific pattern. The fibre or wire may be attached to the inner member or may simply be retained by the struts forming the outer periphery of the bulge 602. Bulge 602 may be formed from three or more struts, and these struts may be generally aligned with the central axis of the device or may be curved or spiraled around this axis as previously shown.

Figure 14A:
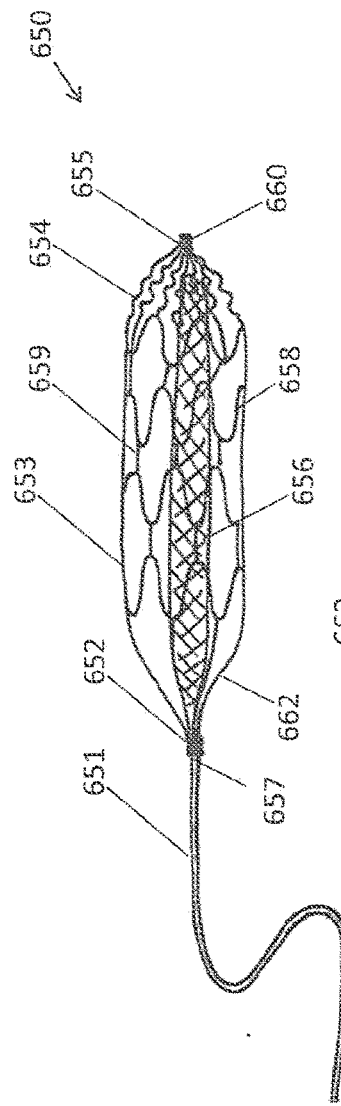
FIG. 14a is a side view of a clot retrieval device of this invention.
Figure 14B:
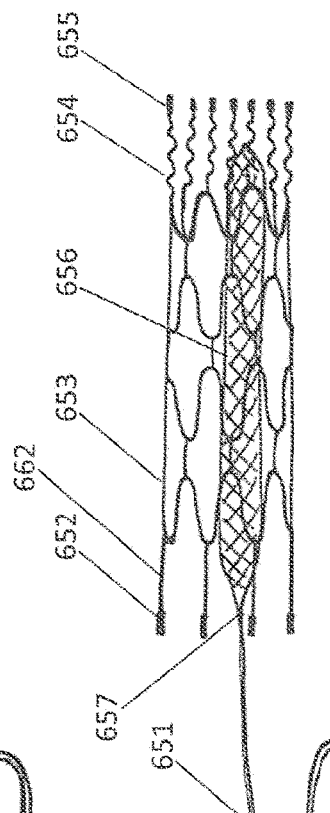
FIGS. 14b to 14d show side views of the clot retrieval device of FIG. 14a in use.
Figure 14C:
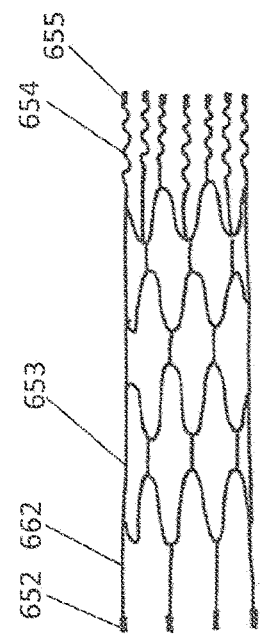
Figure 14D:
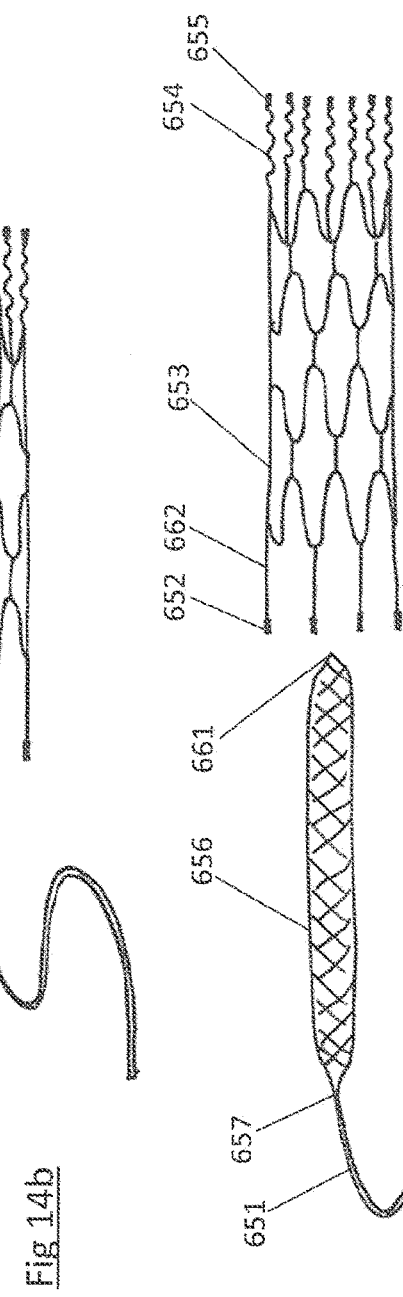

FIG. 14a shows another clot retrieval device 650 of this invention in which the outer expandable member 653 is detachable from the rest of the device. FIG. 14b shows the same device following detachment of the outer member. FIGS. 14c and 14d together show the inner expandable member being retracted from the patient leaving the outer expandable member behind. This detachment feature enables a user to elect to leave the outer member deployed within a vessel as an implant, which might be desirable in the case of an atherosclerotic or thrombotic occlusion, or in the event that the device become so firmly lodge in the clot that the user felt it would be unsafe to pull the entire device any harder. The principles illustrated could be applied to any of the inner and/or outer expandable members shown elsewhere herein. Device 650 comprises an outer expandable member 653 and an inner expandable member 656, both connected to the distal end of an elongate shaft 651 at proximal joint 657. The outer expandable member comprises a plurality of struts 658 and connectors 659, with a series of proximal terminations 652 and distal terminations 655. In the configuration prior to detachment the proximal terminations 652 are attached together and to shaft 651 at proximal joint 657, and the distal terminations 655 are attached together at distal joint 660.

In the embodiment shown the proximal joint 657 is generally concentric with the device and is radially displaced from the side wall of the vessel. Therefore the proximal struts 662 would obstruct the vessel lumen if left unaltered, causing potential recrossing difficulties and acting as a potential nidus for future clot formation. To address this issue the proximal terminations 652 separate upon detachment from the proximal joint 657, freeing the proximal struts (which are heat set to remember a preferred radially outwardly projecting configuration) to expand and appose the vessel wall or clot. A variety of means can be employed to detach the proximal joint and terminations, including: electrolytically, resistance heating of a low melt joining material, or other mechanical pull-wire or twisting mechanism. An example of a pull wire joint is shown in FIG. 16. In another embodiment the proximal joint 657 is offset from the centreline of the device and vessel and is generally in line with the plane of the outer circumference of the outer member, in which case it is not necessary to separate the proximal struts 662 as they will self align with clot and/or vessel wall automatically upon detachment of the proximal joint.

In one embodiment the distal terminations 655 are held together by a bioabsorbable fibre or collar, which is configured to dissolve after a period of time in contact with blood and thus allow the terminations to separate and the distal cone to expand towards a cylindrical shape and appose the vessel wall. This time period is ideally greater than 30 minutes and less than 7 days, and is most preferably between 1 and 3 hours. In other embodiments the distal joint is connected to the distal end 661 of the inner expandable member in such a way that retraction of the inner expandable member relative to the outer expandable member disconnects the distal joint and allows the distal cone of the outer member to expand. In yet other embodiments the distal terminations are released by means similar to that described above for the release of the proximal terminations.

FIGS. 15a-15d show a method of use of a detachable device 700, similar to previously described device 650. Device 700 comprises an outer expandable member 704, an inner expandable member 705, a shaft 709 and a distal net 706. Distal net 706 is attached to the distal end of the inner expandable member 705, and the proximal end of the inner member is attached to the distal region of shaft 709. The proximal end of the outer expandable member is attached to the distal end of the shaft 709 at proximal joint 708, and is detachable in the same manner as that previously described for device 650. The distal end of the outer expandable member differs from that of device 650 in that it terminates in crowns 710 and not in a conical section, and therefore does not require detachment and further expansion if the device is to be left in place as an implant.

The method of use is similar to that described in relation to FIG. 2 and FIG. 7 in that access is gained and a microcatheter 703 is advanced through vessel 701 to and across clot 702 as shown in FIG. 15b. Device 700 is then advanced through the microcatheter and deployed within the clot by retracting the microcatheter to a position proximal of the expandable portion of the device as shown in FIG. 15c. The device and clot can now be retracted together and removed from the patient, or if desired, the user may elect to detach the outer expandable member from the rest of the device at this point. The detachment process is as previously described in relation to FIG. 14b, and results in the outer expandable member apposing the vessel wall and/or clot as shown in FIG. 15d, at which point the remainder of the device is retracted and removed from the patient.

FIG. 16 shows one embodiment of a detachable proximal joint of a device of this invention, such as might be employed with devices 650 or 700 previously described. Proximal strut 756 of the inner expandable member terminates proximally in half collar 757 which is connected (soldered, bonded, welded or other means) to the distal end of shaft 750. Proximal struts 752 and 753 of the outer expandable member terminate proximally in half collars 754 and 755 which sit over the distal end of shaft 750 and are prevented from separating outwardly by pull-wire collar 703, and from slipping distally by the shaft distal step 751. Pull-wire 758 terminates in a pull-wire collar 760 and extends proximally to a point adjacent the proximal end of elongate shaft 750 outside of the patient. Retraction of the pull-wire relative to the shaft retracts the pull-wire collar which allows the half collars 754 and 755 to detach and separate, thus releasing the outer expandable member. In another embodiment the half collar 757 is a full collar and takes the place of step 751 in forming a distal abutment surface against which the split collars 754 and 755 of the outer expandable member lie.

FIG. 17*a* shows a side view of device 800, which is an expandable clot retrieval device configured to self expand to a shape that occupies at least two planes. In the embodiment shown shaft 801 is connected to an expandable body which comprises a proximal section 802, a middle section 804, and a distal net section 805. The middle section 804 comprises a generally cylindrical body including cells 806 from which protrude clot engaging petals 803. The entire expandable body may be formed from a monolithic structure of struts and connectors, and the distal net may be formed from the same structure or may incorporate fibres or wires or a membrane to reduce the pore size of its openings and increase its scaffolding density. Proximal section 802 may be configured with an expanded diameter smaller than that of the body of middle section 804. Petals 803 may be configured to expand outward to a larger diameter than that of the middle body section.

FIG. 17*b* shows a detail view of a portion of the cut pattern of the middle section 804 as it looks prior to expansion. Petals 803 fit within cells 808 and are connected to the cell and body proximally at connectors 808, and are unconnected at distal crowns 807. This design enables a single piece of tubing to be used to manufacture a three dimensional device which can occupy multiple planes when expanded. Thus many of the features and benefits of the dual layer inner and outer expandable member designs described elsewhere can be incorporated in a one piece part. In one embodiment the proximal section 801 and middle body section 804 have the same diameter and function in a similar manner to the inner expandable member described previously, creating a flow channel through the clot and reducing the pressure gradient across the clot, without gripping or exerting any significant force on the vessel wall; while petals 803 engage with and grip the clot to retain it securely for retraction.

FIG. 18 shows the distal end of an inner expandable member similar to part 3 of device 1. This member comprises a framework of struts 854 and connectors 855 forming a proximal body section 853, to which is connected one or more elongate struts 852 configured in a spiral shape and terminating in distal collar 851. This design creates a very compliant spring to accommodate relative movement between this inner expandable member and an outer expandable member or other part to which it might be connected without exerting a strong axial force on the body section 853 which might tend to collapse or reduce its diameter. The pitch, number of struts and number of turns of the spiral section 852 may be varied to alter the compliance and the foreshortening of this section. The diameter of this spiral section might in some embodiments differ from that of the body section 853. In one particular embodiment the spiral section diameter is greater than that of the body section 853 and is similar to that of the outer expandable member. This embodiment could be used in a similar manner to that described for parts 500 and 606, and function as fragment protection filter.

FIG. 19 shows a clot retrieval device 877 partially restrained within a loading tool 875. The Loading Tool 875 comprises a generally tubular body composed of a first material 880 and a second material 876. In the embodiment shown the first material is transparent and the second material is coloured and/or opaque and configured in a spiral stripe around or through the first material. This loading tool can be used to collapse a clot retrieval device or to hold a clot retrieval device in a collapsed state prior to insertion into a microcatheter for delivery to a target location within a patient. The tool can also be used to reload a clot retrieval device for a second use if necessary to remove a stubborn clot, in which case it is advantageous that the tool be easily identifiable, as it may have been dropped onto a sterile table or drape along with numerous other items. The distinctive spiral pattern can be quickly identified even by a stressed and hurried user. It is also advantageous that the first material 880 be transparent or at least translucent so that the position of the clot retrieval device can be identified through the wall of the tool. This is particularly helpful when advancing the device from the loading tool into a microcatheter. It is of further advantage if the outer surface of the tube is of a relatively high coefficient of friction material and the inner surface is of a relatively low coefficient of friction material. The high coefficient of friction outer surface means the tool can be easily gripped by the user and by a rotating haemostasis valve while in use, and the low coefficient of friction inner surface facilitates easy advancement of the clot retrieval device through the tool. This can be achieved by using extruding the base tube from a low coefficient of friction material such as PTFE, and then roughening the surface (by etching or grit blasting or grinding or other such means) or by adding an outer sleeve of a higher friction material such as PET or Polyolefin for example. Preferably this sleeve or roughening is not applied to the distal few centimetres of the tool, to avoiding impacting on its transparency.

FIG. 20 shows a portion of the body section of an inner expandable member somewhat similar to part 3 of device 1. This body section comprises a series of ring elements 901 connected to one another by connector elements 902, forming closed cells 908. Each cell has a proximal apex 900 and a distal apex 907. Each ring element is offset from each neighbouring ring element such that the apices 900 and 907 are offset from each other relative to the central axis of the member. This offset provides for greater bending flexibility in the member because in addition to flexing of the struts forming each cell, the connectors themselves can flex to accommodate a bend in this offset design. Line 905 is an axis through the proximal apex of cell 908 parallel to the axis of the member. Line 904 is an axis through the distal apex of cell 908 parallel to the axis of the member. Thus the perpendicular distance between lines 904 and 905 represents the offset between adjacent ring elements. Lines 909 and 910 are lines through the proximal and distal ends of connector 902, perpendicular to the central axis of the expandable member. Thus the perpendicular distance between lines 909 and 910 represents the axial spacing between the ring elements. In one embodiment the distance between lines 904 and 905 is less than that between lines 909 and 910. In another embodiment the distance between lines 904 and 905 is equal to that between lines 909 and 910. In one embodiment the distance between lines 904 and 905 is greater than that between lines 909 and 910. In general it is desirable to maximise the offset and minimize the spacing in order to achieve an optimal balance between clot scaffolding and device flexibility.

FIGS. 21*a* and 21*b* show an alternative embodiment of an outer expandable member such as part 2 of FIG. 1. FIG. 21*a* illustrates a side view of the outer member and FIG. 21b shows the barrel section of the outer member unrolled into a 2D configuration. In this embodiment the proximal collar 970 is connected to proximal struts which in turn are connected to a series of struts that form cells along the body section of the device. These cells are configured to act as large inlet windows 973, 978, 979, 983, 984, 985, or smaller highly scaffolded cells 972, 977, 980, 981, 982. The large inlet window cells facilitate movement of the clot into the outer member and into the reception space between the outer member and inner tubular member. The smaller highly scaffolded cells engage with the clot and help dislodge the clot from the vessel. They also promote the movement of the clot from the highly scaffolded areas into the inlet windows of the device.

The distribution of the large inlet windows and smaller cells is key to the performance of the device and in this configuration the large inlet windows and smaller scaffolded cells are generally alternated along the length of the device, for example large cell 973 is adjacent to smaller cell 977 which is adjacent to larger cell 978 which is adjacent to smaller cell 980, along the length of the device. In this configuration the larger inlet windows and pairs of smaller scaffolded cells are also generally alternated radially around the circumference of the device. For example large inlet window 978 is adjacent to smaller cells 981 and 982 which are adjacent to large inlet window 983 around the circumference of the outer member.

In this embodiment the proximal struts 971 are connected to a ring of smaller scaffolded cells 972 around the proximal end of the outer member. The distal end of the body section may be connected to a ring of struts 974 that provide sufficient radial force to prevent the movement of clot past the distal end of the device during retraction in the vessel. The distal ring of struts 974 is connected to a series of struts 975 which form a closed end on the outer member and terminate at the distal collar 976.

It will be apparent from the foregoing description that, while particular embodiments of the present invention have been illustrated and described, various modifications can be made without departing from the spirit and scope of the invention. Accordingly, it is not intended that the present invention be limited and should be defined only in accordance with the appended claims and their equivalents.

The invention claimed is:

1. A clot retrieval device for removing clot from a blood vessel, comprising:
    a framework of struts forming a porous inner body flow channel and having a tubular main body portion and a distal portion; and
    a framework of struts forming an outer body radially surrounding the tubular main body portion of the inner body during both the collapsed delivery configuration and the expanded deployed configuration, the outer body comprising:
    a first scaffolding segment with a plurality of cells,
    a second scaffolding segment with a plurality of cells and distal of the first scaffolding segment, the porous inner body flow channel extending inside the first and second scaffolding segments;
    wherein the outer body is expandable to a radial extent greater than the porous inner body flow channel to define an inlet mouth between the first and second scaffolding segments and the porous inner body flow channel, the inlet mouth being larger than the cells of the second scaffolding segment;
    wherein the distal portion of the porous inner body flow channel being located within the outer tubular body and adjacent a distal end portion of the outer tubular body, and extending in the deployed configuration towards the tubular main body to a greater extent than the tubular main body portion.

2. The device of claim 1, wherein a porosity provided by the plurality of struts of the porous inner body flow channel is greater than a porosity provided by the plurality of struts of the outer body.

3. The device of claim 1, further comprising: an elongate member having a distal end coupled to a proximal end of at least one of the porous inner body and the outer tubular body at a connection point.

4. The device of claim 3, wherein the connection point is radially offset relative to a longitudinal axis of the outer tubular body.

5. The device of claim 1, wherein adjacent struts of the framework of struts that form the porous inner body define inner body cells, wherein adjacent struts of the framework of struts of the outer tubular body define outer body cells, wherein the outer tubular body cells are larger than the porous inner body cells.

6. The device of claim 1, wherein the framework of struts that form the outer tubular body define a plurality of strut segments, wherein the outer tubular body further includes at least one clot inlet mouth positioned between adjacent strut segments.

7. The device of claim 1, wherein the inlet mouth is eccentrically arranged about a longitudinal axis of the outer tubular body.

8. The device of claim 1, the distal end portion of the outer tubular body tapers distally.

9. The device of claim 1, further comprising a shaft having a distal end coupled to a proximal end of the inner body.

10. A clot retrieval device for removing clot from a blood vessel, comprising:
    a framework of struts forming an inner body having a tubular main body portion in an expanded configuration and a distal portion;
    a framework of struts forming an outer tubular body radially surrounding the main body portion of the inner body during both the collapsed delivery configuration and the expanded deployed configuration and including a distal end portion, the distal portion of the inner body extending in the expanded configuration towards the outer tubular body to a greater extent than the main body portion, the outer tubular body comprising:
    a first scaffolding segment with a plurality of cells,
    a second scaffolding segment with a plurality of cells and distal of the first scaffolding segment, the inner body extending inside the first and second scaffolding segments;
    wherein the outer body is expandable in the expanded configuration to a radial extent 50% greater than the inner body to define in a longitudinally-extending clot inlet mouth between the first scaffolding segment, the second scaffolding segment, and the inner body, the inlet mouth being larger than the cells of the second scaffolding segment.

11. The device of claim 10, wherein a porosity provided by the framework of struts of the inner body is greater than a porosity provided by the framework of struts of the outer tubular body.

12. The device of claim 10, further comprising: an elongate member having a distal end coupled to a proximal end of at least one of the inner body and the outer tubular body at a connection point.

13. The device of claim 12, wherein the connection point is radially offset relative to a longitudinal axis of the outer tubular body.

14. The device of claim 10, wherein adjacent struts of the framework of struts that form the inner body define inner body cells, wherein adjacent struts of the framework of struts of the outer tubular body define outer body cells, wherein the outer tubular body cells are larger than the porous inner body cells.

15. The device of claim 10, wherein the inlet mouth is eccentrically arranged about a central longitudinal axis of the outer tubular body.

16. The device of claim 10, the distal end portion of the outer tubular body tapers distally.

17. The device of claim 10, further comprising a shaft having a distal end coupled to a proximal end of the inner body.

* * * * *